Figure 1:
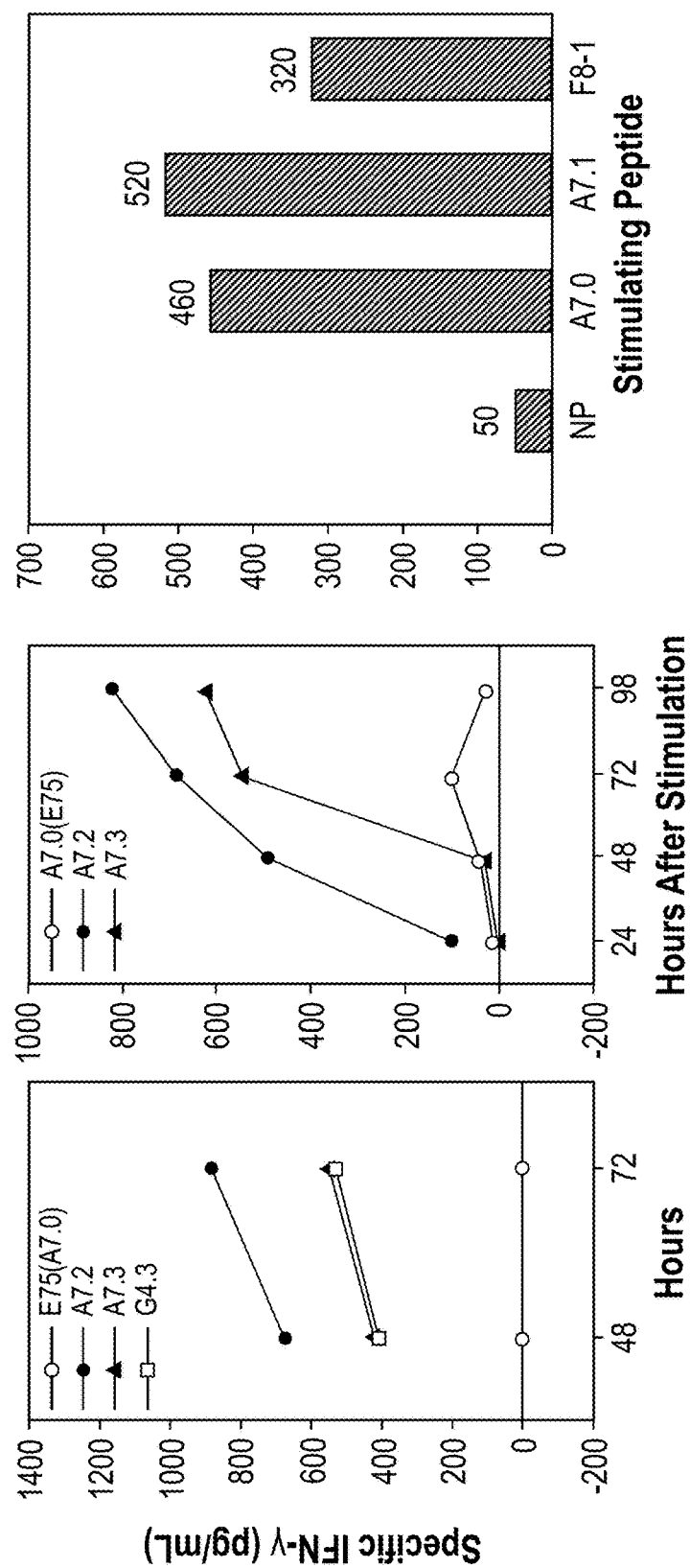

US010239916B2

(12) United States Patent
Ioannides et al.

(10) Patent No.: US 10,239,916 B2
(45) Date of Patent: Mar. 26, 2019

(54) CONTROLLED MODULATION OF AMINO ACID SIDE CHAIN LENGTH OF PEPTIDE ANTIGENS

(71) Applicants: Board of Regents, The University of Texas System, Austin, TX (US); Henry M. Jackson Foundation for the Advancement of Military Medicine, Inc., Rockville, MD (US)

(72) Inventors: Constantin G. Ioannides, Houston, TX (US); Martin L. Campbell, Colorado Springs, CO (US); Catherine A. O'Brian, Chicago, IL (US); George E. Peoples, San Antonio, TX (US)

(73) Assignees: Board of Regents, The University of Texas Systems, Austin, TX (US); Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 459 days.

(21) Appl. No.: 14/445,776

(22) Filed: Jul. 29, 2014

(65) Prior Publication Data

US 2015/0175660 A1 Jun. 25, 2015

Related U.S. Application Data

(62) Division of application No. 10/507,009, filed as application No. PCT/US03/06952 on Mar. 6, 2003, now Pat. No. 8,802,618.

(60) Provisional application No. 60/362,778, filed on Mar. 8, 2002, provisional application No. 60/412,441, filed on Sep. 20, 2002.

(51) Int. Cl.
 *C07K 7/06* (2006.01)
 *C07K 14/47* (2006.01)
 *C07K 14/74* (2006.01)

(52) U.S. Cl.
 CPC .......... *C07K 7/06* (2013.01); *C07K 14/4705* (2013.01)

(58) Field of Classification Search
 None
 See application file for complete search history.

(56) References Cited

U.S. PATENT DOCUMENTS

| | | |
|---|---|---|
| 4,433,092 A | 2/1984 | Nemeth |
| 4,554,101 A | 11/1985 | Hopp |
| 4,631,211 A | 12/1986 | Houghten |
| 4,631,221 A | 12/1986 | Disselbeck |
| 4,708,781 A | 11/1987 | Poorten |
| 4,708,871 A | 11/1987 | Geysen |
| 4,833,092 A | 5/1989 | Geysen |
| 5,194,392 A | 3/1993 | Geysen |
| 5,480,971 A | 1/1996 | Houghten et al. |
| 5,550,214 A | 8/1996 | Eberlein et al. |
| 6,075,122 A | 6/2000 | Cheever |
| 6,127,524 A | 10/2000 | Casipit et al. |
| 6,338,945 B1 | 1/2002 | Nicolette |

OTHER PUBLICATIONS

Rodkey. uth.tmc.edu/pathology/medic/immunology/Immuno/AgImmunogen07.pdf, 2010, pp. 1-25.*
Karin et al (J. Exp. Med., 1994, 180, 2227-2237).*
Alexander-Miller, M.A. et. al., "Role of the antigen, CD8, and cytotoxic T lymphocyte (CTL) avidity in high dose antigen induction of apoptosis of effector CTL," *The Journal of Experimental Medicine*, 184:485-492, 1996.
Anderson et al., "Peptide priming of cytolytic activity to her-2 epitope 369-377 in healthy individuals," *Clin. Cancer Res.*, 6:4192-4200, 2000.
Baker et al., "Conversion of a t cell antagonist into an agonist by repairing a defect in the tcr/peptide/mhc interface: implications for tcr signaling," *Immunity*, 13:475-484, 2000.
Berman et al., "The Protein Data Bank," *Nucleic Acids Research*, 28:235-242, 2000.
Broome et al., "Expression of Bcl-2, Bcl-x, and Bax after T cell activation and IL-2 withdrawal", *J Immunol*, 155:2311-7, 1995.
Brutlag et al., "Improved sensitivity of biological sequence database searches," *Comput. Appl. Biosci.*, 6(3):237-245, 1990.
Carter, Darrick et al. "Induction of cancer immunity by targeted hydrophobic ladders in the tumor antigen," *FASEB Journal*, Database Accession No. PREV200100264680, Mar. 8, 2001.
Castilleja et al., "Induction of tumor-reactive CTL by C-side chain variants of the CTL epitope Her-2/neu protoonocogene (369-377) selected by

(56) References Cited

OTHER PUBLICATIONS

DiSomma et al., "TCR engagement regulates differential responsiveness of human memory t cells to fas (cd95)-mediated apoptosis," *J. Immunol.*, 162:3851, 1999.
Dutoit, V. et. al., "Heterogeneous T-cell response to MAGE-A10 (254-262): high avidity-specific cytolytic T lymphocytes show superior antitumor activity," *Cancer Research*, 61:5850-5856, 2001.
Eberl et al., "MHC class I H-2Kd-restricted antigenic peptides: additional constraints for the binding motif," *Int. Immunol.*, 5(11): 1489-1492, 1993.
Falk et al., "Allele-specific motifs revealed by sequencing of self-peptides eluted from mhc molecules," *Nature*, 351:290, 1991.
Fetrow and Bryant, "New programs for protein tertiary structure prediction," Biotechnology, 11(4):479-484, 1993.
Fisk et al., "Identification of an immunodominant peptide of her-2/neu protooncogene recognized by ovarian tumor-specific cytotoxic t lymphocyte lines," *J. Exp. Med.*, 181:2109-2117, 1995.
Fisk et al., "Mass-spectrometric analysis of naturally processed peptides recognized by ovarian tumor-associated cd8+ ctl," *Int. J. Oncol.*, 10:159-169, 1997.
Garboczi et al., "Structure of the complex between human t-cell receptor, viral peptide and hla-a2," *Nature*, 384:134-141, 1996.
Geysen et al., "Use of peptide synthesis to probe viral antigens for epitopes to a resolution of a single amino acid," *Proc. Natl. Acad. Sci., USA*, 81:3998-4002, 1984.
Gillogly et al., "Induction of immunity to her-2 by tcr directed variants of the ctl epitope e75," *FASEB J.*, 14:A147.18, 2000.
Haskell-Luevano et al., "β-Methylation of the Phe7 and Trp9 melanotropin side chain pharmacophores affects ligand-receptor interactions and prolonged biological activity," *J. Med. Chem.*, 40:2740-2749, 1997.
Hausman et al., "Peptide recognition by two hla-a2/tax$_{11-19}$-specific t cell clones in relationship to their mhc/peptide/tcr crystal structures," *J. Immunol.*, 162:5389, 1999.
Houghten et al., "A completely sunthetic toxoid vaccine containing *escheichia coli* heat-stable toxin and antigenic determinants of the heat-labile toxin b subunit," *Infection and Immunity*, 48:735-740, 1985.
Houghten, "General method for the rapid solid-phase synthesis of large numbers of peptides: specificity of antigen-antibody interaction at the level of individual amino acids," *Proc. Natl. Acad. Sci., USA*, 82:5131-5135, 1985.
Hruby et al., "Topographically designed analogues of [D-Pen, D-Pen5]enkephalin," *J Med. Chem.*, 34:1823-1830, 1991. Hruby et al., "Topographically designed analogues of [D-Pen, D-Pen5]enkephalin," *J. Med. Chem.*, 34:1823-1830, 1991.
Jameson and Wolf, "The antigenic index: a novel algorithm for predicting antigenic determinants," *Comput Appl Biosci*, 4(1):181-186, 1988.
Kirchhoff et al., "TCR-mediated up-regulation of c-flip$_{short}$ correlates with resistance toward cd95-mediated apoptosis by blocking death-inducing signaling complex activity," *J. Immunol.*, 165:6293, 2000.
Knutson et al., "Immunization with a her-2/neu helper peptide vaccine generates her-2/neu cd8 t-cell immunity in cancer patients," *J. Clin. Invest*, 107:477, 2001.
Krammer, "CD95's deadly mission in the immune system," *Nature*, 407:789-795, 2000.
Lee et al., "Identification of activated tumor antigen-reactive cd8+ cells in healthy individuals," *Oncol. Reports*, 7:455-466, 2000.
Lu and Celis, "Use of two predictive algorithms of the world wide web for the identification of tumor-reactive t-cell epitopes," *Cancer Res.*, 60(18):5223-5227, 2000.
Madden et al., "The antigenic identity of peptide-mhc complexes: a comparison of the conformations of five viral peptides presented by hla-a2," *Cell*, 75:693-708, 1993.
Madden, "The three-dimensional structure of peptide-MHC complexes", *Annu Rev Immunol*, 13:587-622, 1995.

Mueller et al., Differential regulation of bcl-2 and bcl-x by CD3, CD28, and the IL-2 receptor in cloned CD4+ helper T cells. A model for the long-term survival of memory cells, *J. Immunol*, 156:1764-71, 1996.
Office Action issued in U.S. Appl. No. 10/507,009, dated Apr. 5, 2013.
Office Action issued in U.S. Appl. No. 10/507,009, dated Feb. 3, 2010.
Office Action issued in U.S. Appl. No. 10/507,009, dated Jun. 6, 2007.
Office Action issued in U.S. Appl. No. 10/507,009, dated Jun. 21, 2012.
Office Action issued in U.S. Appl. No. 10/507,009, dated Mar. 21, 2011.
Office Action issued in U.S. Appl. No. 10/507,009, dated May 28, 2009.
Office Action issued in U.S. Appl. No. 10/507,009, dated Nov. 20, 2013.
Office Action issued in U.S. Appl. No. 10/507,009, dated Oct. 12, 2012.
Office Action issued in U.S. Appl. No. 10/507,009, dated Oct. 28, 2008.
Office Action issued in U.S. Appl. No. 10/507,009, dated Sep. 16, 2010.
Parker et al., "Scheme for ranking potential hla-a2 binding peptides based on independent binding of individual peptide side-chains," *J. Immunol.*, 153:163, 1994.
PCT International Preliminary Examination Report issued in International Application No. PCT/US2003/006952, completed Aug. 6, 2004.
PCT International Search Report issued in International Application No. PCT/US2003/006952, dated Dec. 23, 2003.
Peitsch et al., "Large-scale protein modelling and intgration with the swiss-prot and swiss-2d page databases: the example of *escherichia coli,*" *Electrophoresis*, 18:498, 1997.
Rammensee et al., "SYFPEITHI: database for mhc ligands and peptide motifs," *Immunogenetics*, 50:213-219, 1999.
Rongcun et al., "Identification of new her2/neu-derived peptide epitopes that can elicit specific ctl against autologous and allogeneic carcinomas and melanomas," *J. Immunol.*, 163:1037-1044, 1999.
Roy and Nicholson, "Cross-talk in cell death signaling," *J. Exp. Med.*, F21-25, 2000.
Saper et al., "Refined structure of the human histocompatibility antigen hla-a2 at 2.6 A resolution," *J. Mol. Biol.*, 219:277, 1999.
Simon et al., "Modeling mhc class II molecules and their bound peptides as expressed at the cell surface," *Mol. Immunol.*, 38(9):681-687, 2002.
Spencer and Braciale, "Incomplete cd8+ t lymphocyte differentiation as a mechanism for subdominant cytotoxic t lymphocyte responses to a viral antigen," *J Exp Med*, 191:1687-1698, 2000.
Stern and Wily, "Antigenic peptide binding by class I and class II histocompatibility proteins," *Structure*, 2:245-251, 1994.
Supplementary European Search Report issued in European Application No. 03723688.2, dated May 12, 2010.
Thomas et al., "The structure, metabolism and function of the carcinoembryonic antigen gene family," *Biochim. Biophys. Acta*, 1032:177, 1990.
Van der Zee et al., "Efficient mapping and characterization of a t cell epitope by the simultaneous synthesis of multiple peptides," *Eur. J Immunol.*, 19:43-47, 1989.
Wallace et al., "Mechanisms of adoptive immunotherapy: improved methods for in vivo tracking of tumor-infiltrating lymphocytes and lymphokine-activated killer cells," *Cancer Res.*, 53:2358-2367, 1993.
Ward et al., "Oxidant-induced s-glutathiolation inactivates protein kinase c-α (pkc-α): a potential mechanism of pkc isozyme regulation," *Biochemistry*, 39:10319, 2000.
Warner et al., "Induction of HIV-specific ctl and antibody responses in mice using retroviral vector-transduced cells," *AIDS Res. and Human Retroviruses*, 7:645-655, 1991.
Weidmann et al., "Relevance of the t cell receptor for immunotherapy of cancer," *Cancer Immunol. Immunother.*, 39:1-14, 1994.

(56) References Cited

OTHER PUBLICATIONS

Weinberger et al., "Identification of human glucocorticoid receptor complementary dna clones by epitope selection," *Science*, 228:740-742, 1985.

Williams et al., "A kinetic threshold between negative and positive selection based on the longevity of the t cell receptor-ligand complex," *J. Exp. Med.*, 189:1531-1544, 1999.

Wolf et al., "An integrated family of amino acid sequence analysis programs," *Comput. Appl. Biosci.*, 4(1):187-191, 1988.

Zaks and Rosenberg, "Immunization with a peptide epitope (p. 369-377) from her-2/neu leads to peptide-specific cytotoxic t lymphocytes that fail to recognize her-2/neu+ tumors," *Cancer Res.*, 58:4902-4908, 1998.

Zum Buschenfelde et al., "Generation of tumor-reactive ctl against the tumor-associated antigen her2 using retrovirally transduced dendritic cells derived from cd34+ hemopoietic progenitor cells," *J. Immunol.*, 165:4133-4140, 2000.

\* cited by examiner

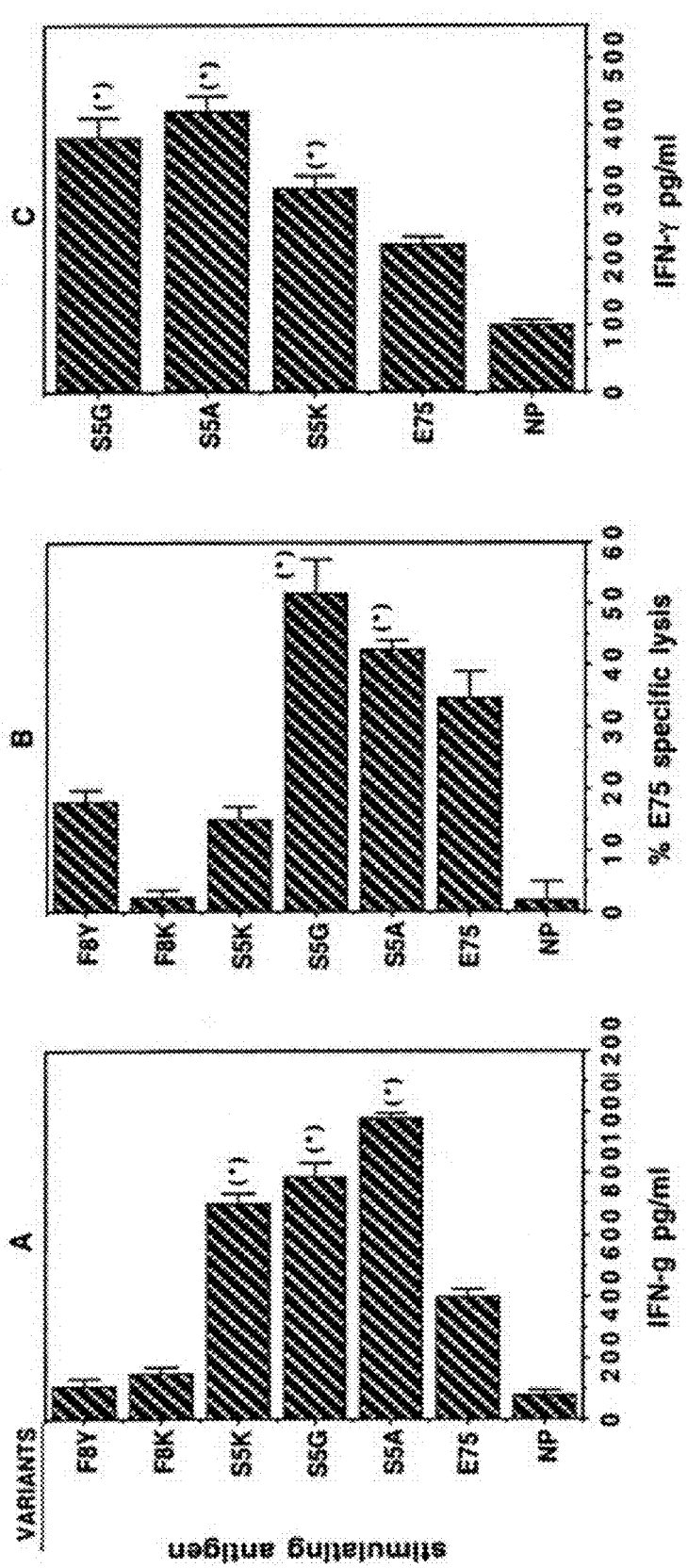
FIG. 8A-C

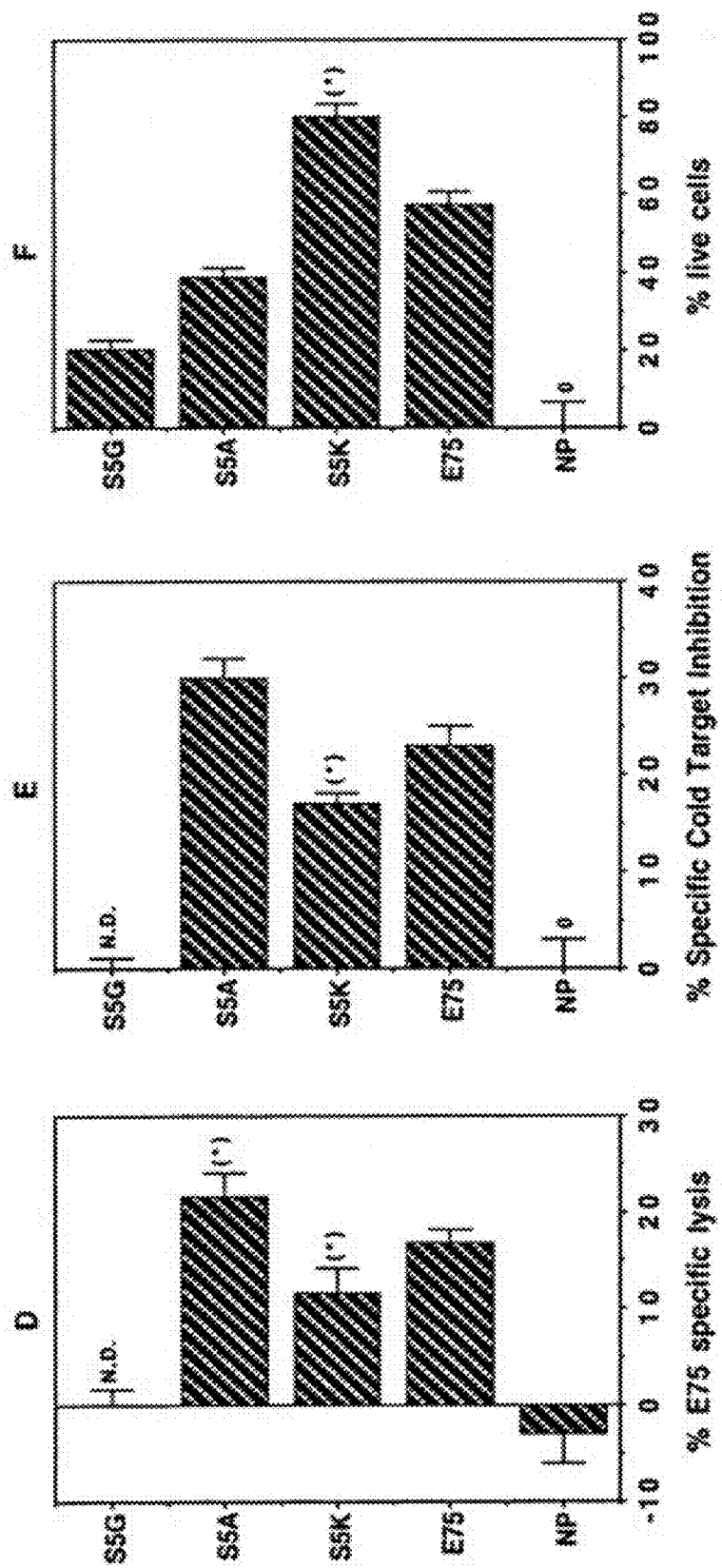
FIG. 8D-F

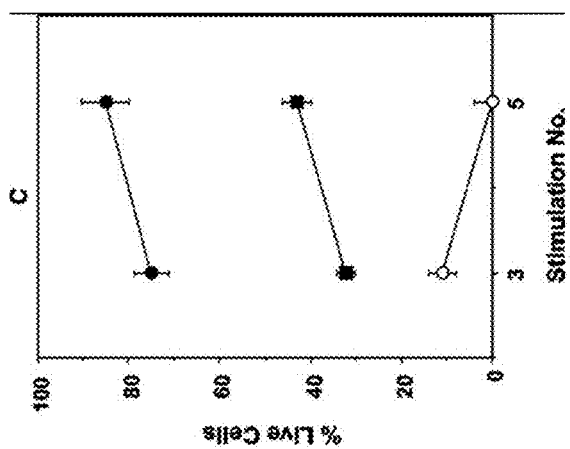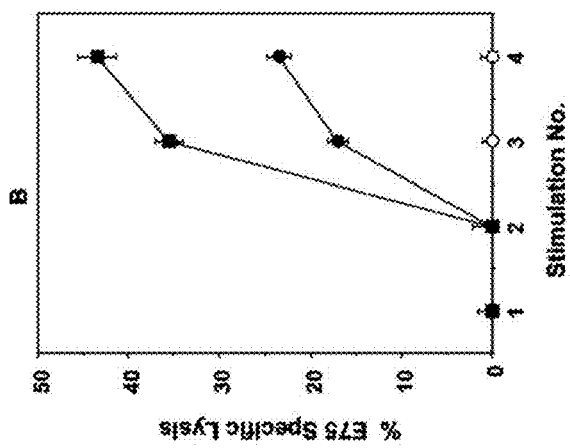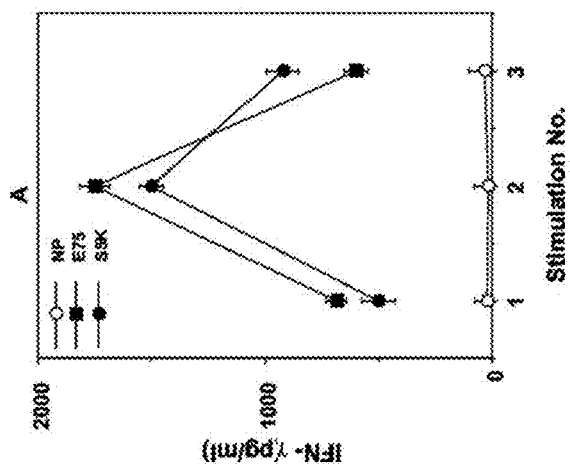
FIG. 9A-C

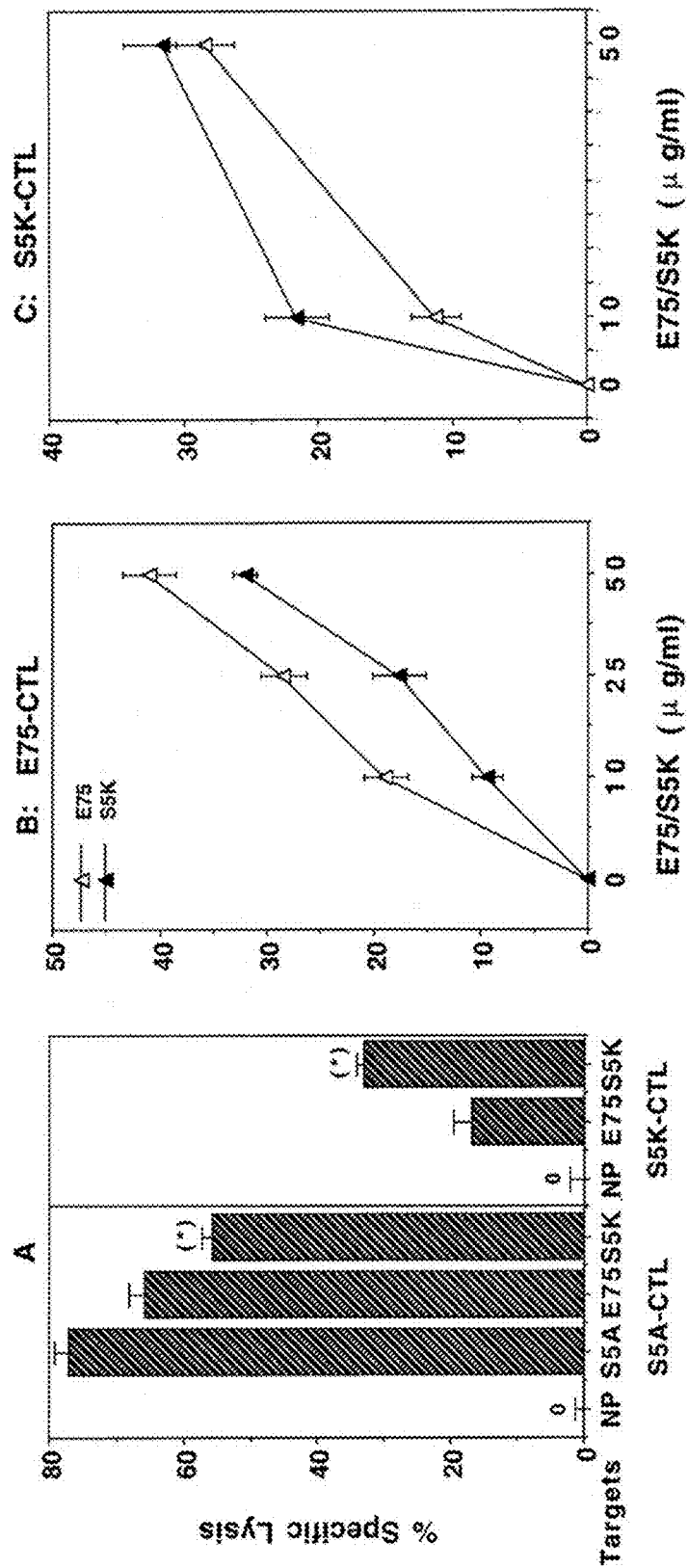
FIG. 10A-C

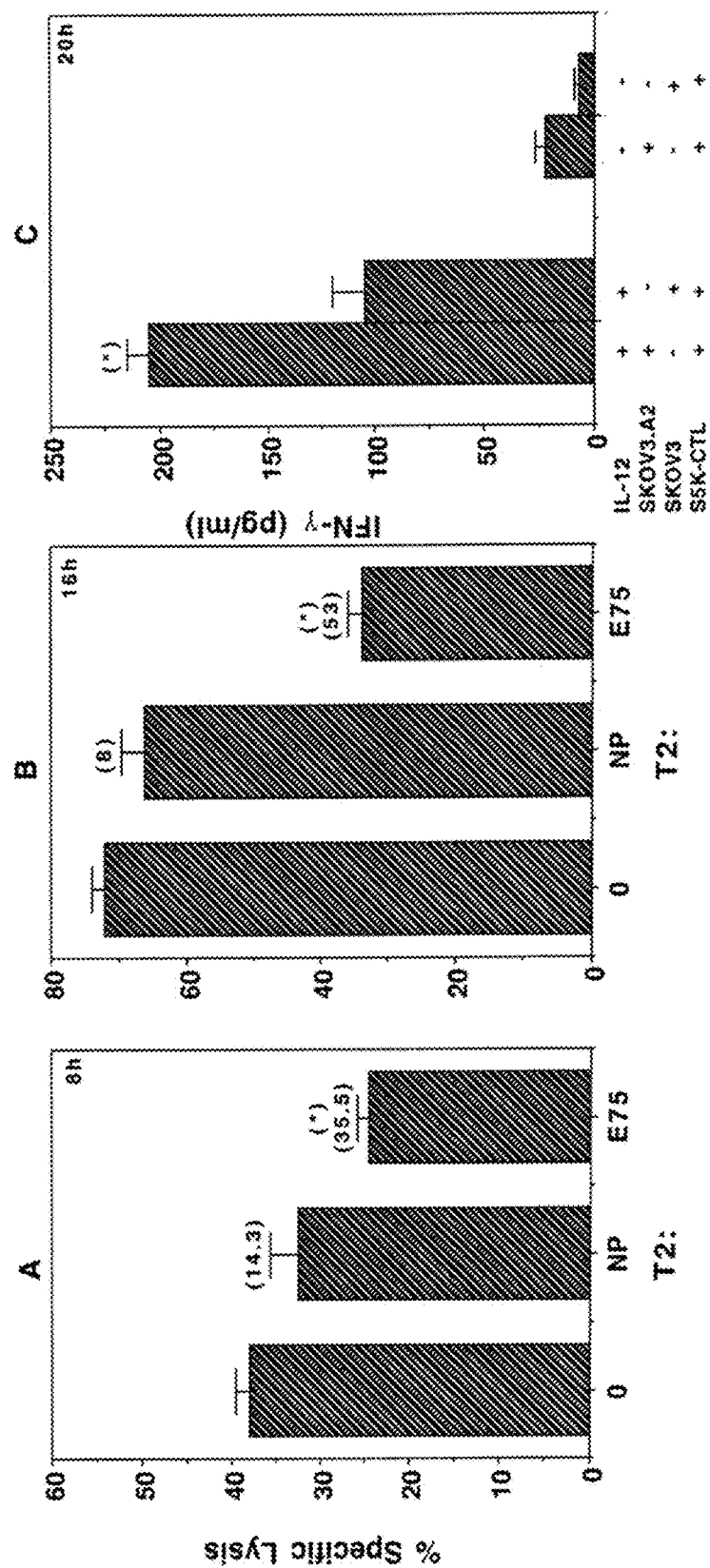
FIG. 11A-C

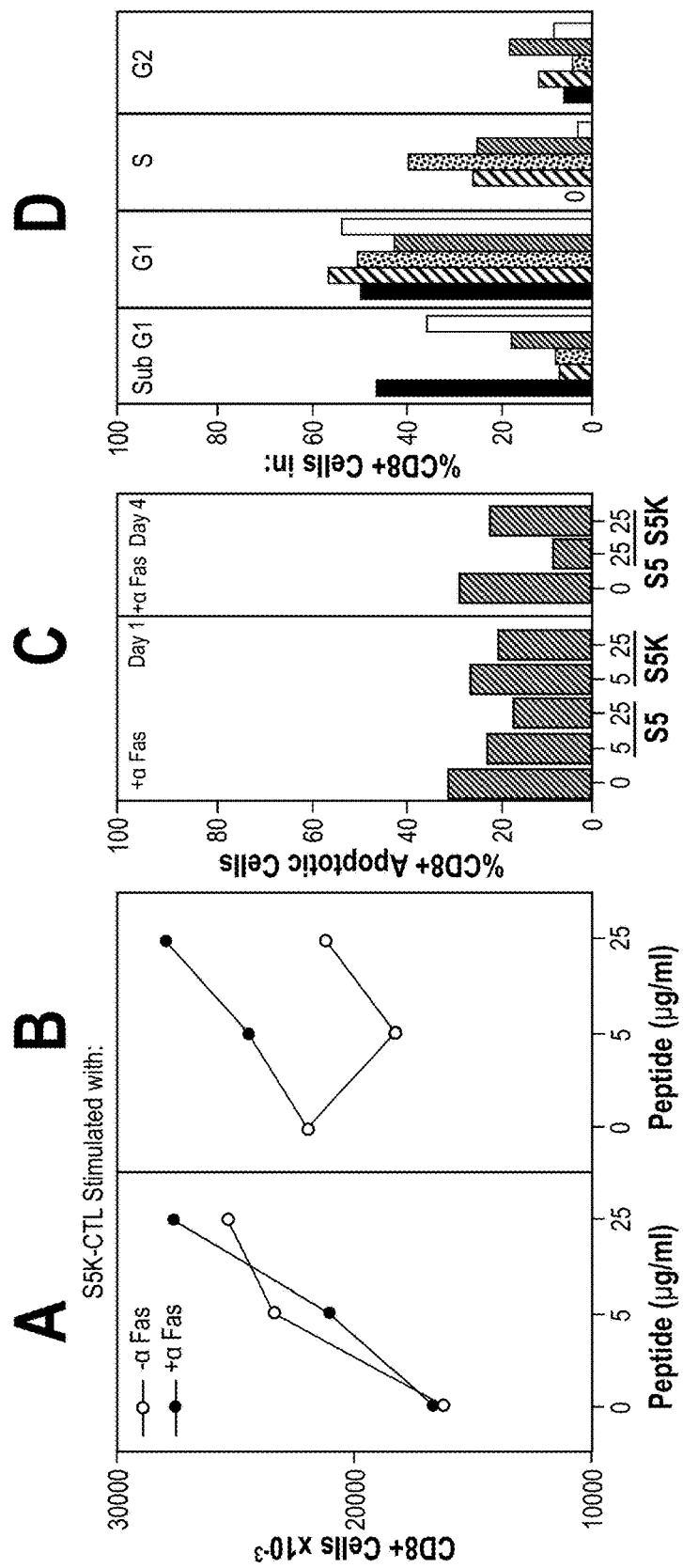
Fig. 12A-D

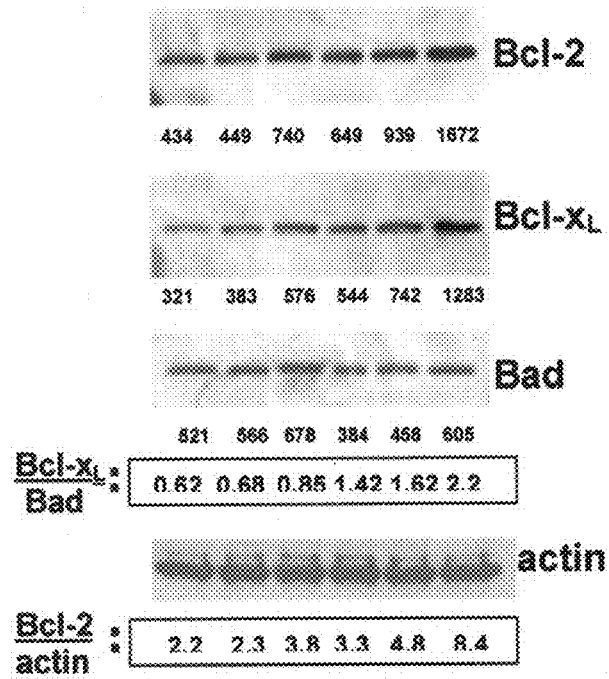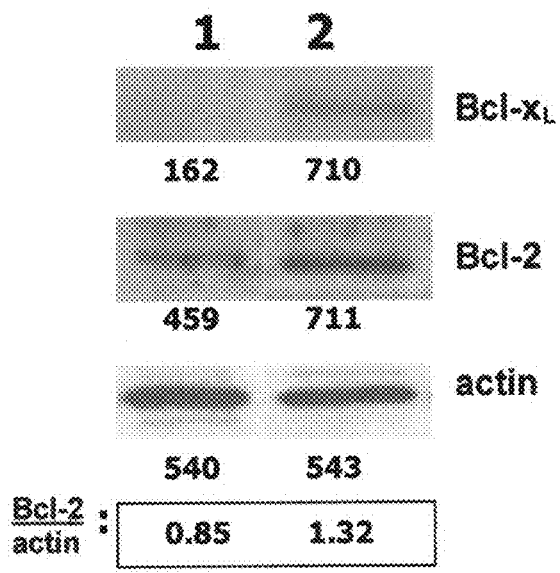
Fig. 13A-B

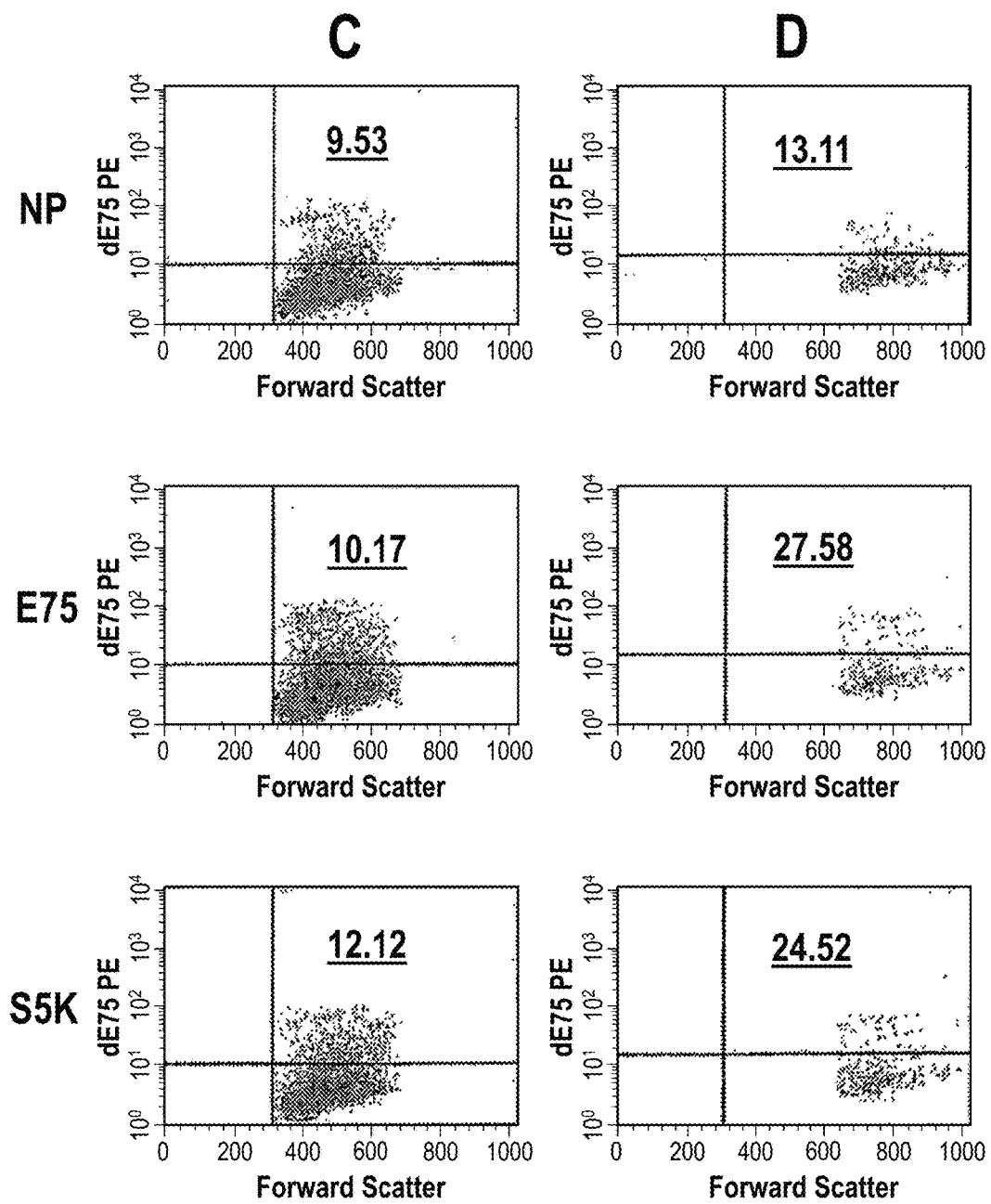
Fig. 13C-D

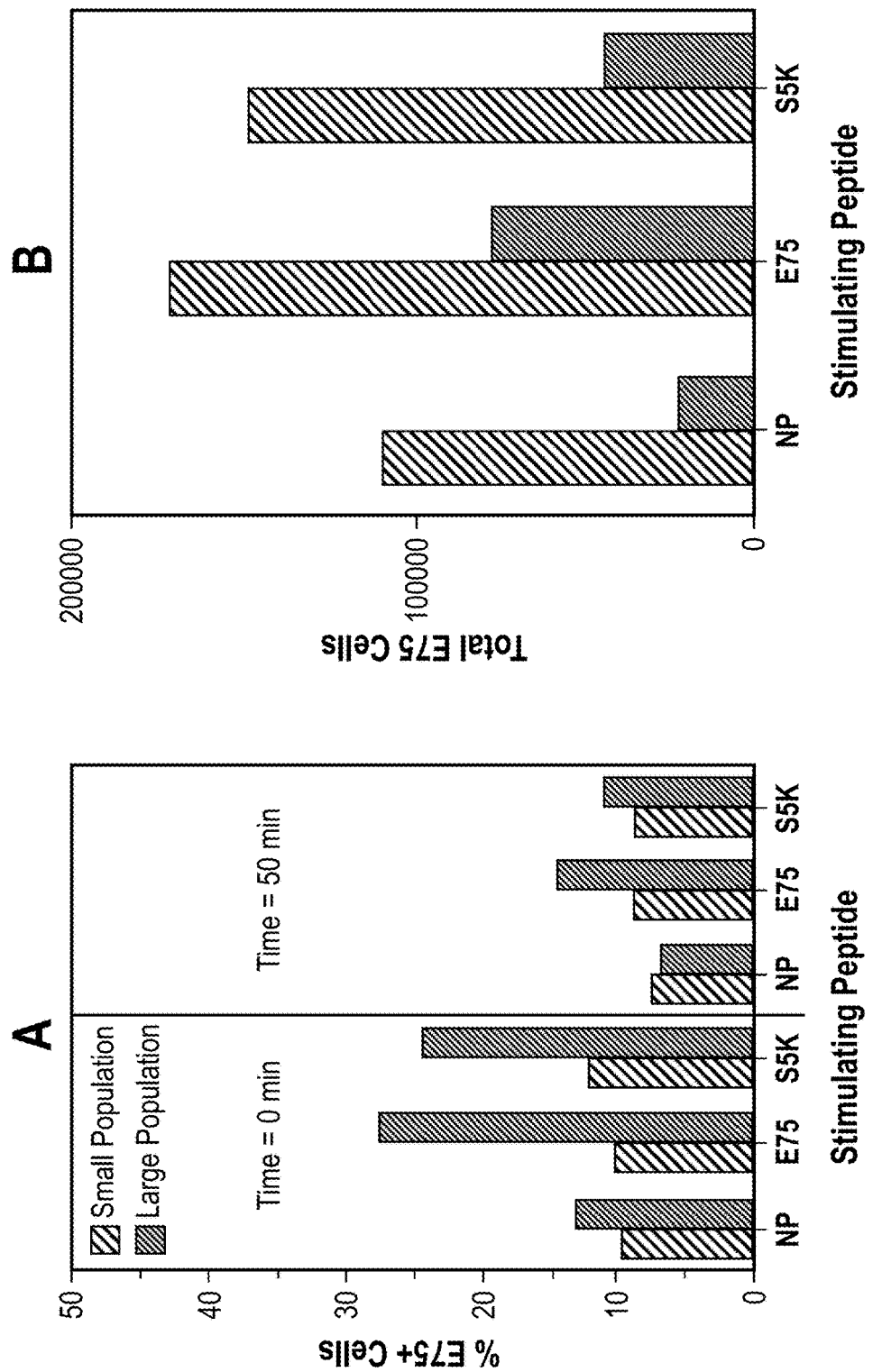
Fig. 14A-B

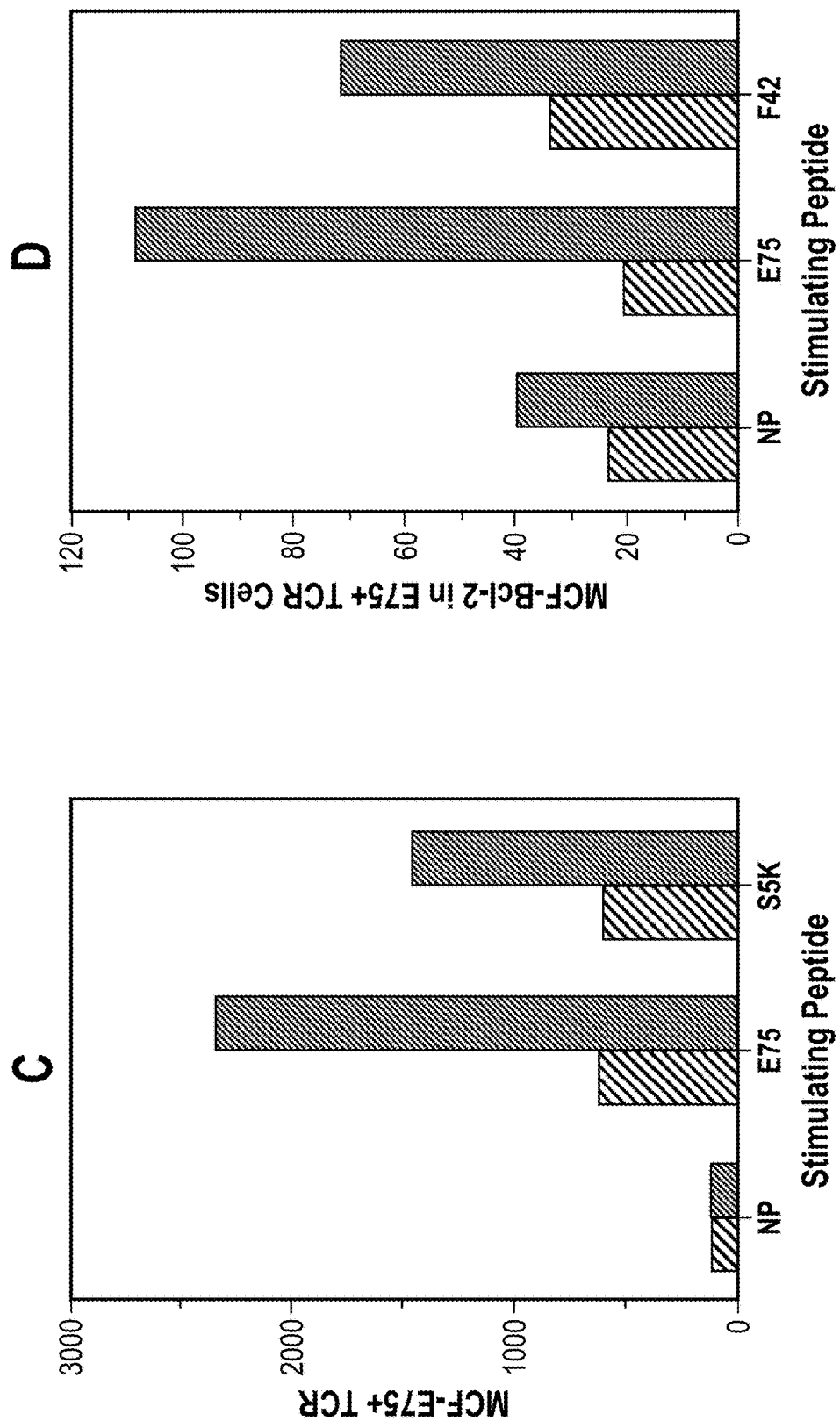
Fig. 14C-D

CONTROLLED MODULATION OF AMINO ACID SIDE CHAIN LENGTH OF PEPTIDE ANTIGENS

This application is a divisional of U.S. application Ser. No. 10/507,009, filed Mar. 28, 2005, which is a national stage application under 35 U.S.C. § 371 of International Application No. PCT/US03/06952, filed Mar. 6, 2003, which claims priority to U.S. Provisional Patent Application Ser. Nos. 60/362,778, filed Mar. 8, 2002, and 60/412,441, filed Sep. 20, 2002, each of which is incorporated in its entirety by reference.

This invention was made with Government support under grant numbers 17-97-I 7098 and I-01-299 awarded by the Department of Defense. The Government has certain rights in the invention.

BACKGROUND OF THE INVENTION

1. Field of the Invention

The present invention relates generally to the fields of immunology and cancer biology. More particularly, it concerns modified peptide antigen compositions and methods of use therefor.

2. Description of Related Art

Immunotherapy refers to the technique of using a patient's immune system against tumor cells or infectious organisms. With respect to cancer, the objective is to direct the patient's immune system against tumor cells by targeting antigens (Ag) that are specific to or preferentially expressed by tumor cells. These antigens thus represent a potential target for methods and compositions of immunotherapy. However, some antigens are present either in low levels in normal cells or in fetal development. For example, oncofetal antigen is a carcinoembryonic antigen (CEA) which is expressed in fetal development and in most adenocarcinomas of entodermally-derived digestive system epithelia, as well as in breast tumor cells and non-small-cell lung cancer cells (Thomas et al., 1990).

As tumor antigen are self-antigen, they are recognized with low-affinity by both cytotoxic T lymphocytes-tumor infiltrating lymphocytes (CTL-TIL) and vaccination-induced CTL, because high avidity (hi-av) CTL are silenced. In addition to being weak immunogens, the effectors induced by antigen variants are often cross-reactive rather than specific for the tumor antigen. A second limitation of the antigen of the type used above is that the tumor antigen is presented in small amounts, in part due to the decreased levels of MHC-I expressed by the tumor compared with healthy tissue. Thus, although a number of approaches have been developed recently for tumor vaccination, these approaches have failed to show significant effects both on cure-rate, and immunological responses to vaccine treatment in patients. This poor immunogenicity requires novel methods to improve the immunogenicity of the tumor antigen.

Typically, the induction of tumor immunity by functional CTL requires: (1) expansion of "naive" or "stand-in" precursors of effector CTL (eCTL) to increase the pool of responders to tumor. This is because disease progression may expand tumor cells to very high numbers, thus only a large pool of CTL precursors can assure expansion of eCTL to similarly high numbers, without exhaustion due to end-stage proliferation and differentiation (2) generation of hi-av eCTL which recognize even small amounts of antigen on tumor; (3) protection of hi-av eCTL from deletion (elimination) at re stimulation with antigen and cytokines; and (4) induction of hi-av memory CTL (mCTL), from eCTL or activated CTL.

Recent advances provided partial answers to the first and second requirements by: (1) expanding precursors of CTL for model antigen using weak and null agonists; (2) identifying hi-av CTL in melanoma, although in small numbers. The other requirements, hi-av CTL protection from elimination and induction of mCTL, are still poorly understood. However, novel approaches are needed to induce, to protect from apoptosis, and to direct hi-av CTL to the memory pool, as shifting the response to low-affinity CTL or non-specific effectors occurs when enhancer antigen generated by sequence changes induce cross-reactive CTL.

Developing successful immunotherapies, including cancer therapies, thus imposes significant constraints for CTL induction, because of (a) the tolerance and anergy induced by inappropriate antigen stimulation plus type II cytokines; (b) the predominance of low-affinity CTL in the periphery: either escaped from tolerance, or induced by antigen and their agonists (an increase in the number of eCTL may not compensate for their low affinity for tumors); (c) the limited understanding of the relationship between the activation of TCR signaling, cytokine signaling and activation of survival pathways in mCTL; (d) costimulatory molecules, cytokine receptors and death receptors are not clone specific; (e) induction of memory cells requires either weaker costimulation and/or a slower rate of proliferation of activated CTL than that of effector CTL; and (f) survival effects are mediated by CD95 and Bcl-2 family pathways. Therefore, there is a need for novel methods and compositions for modulating a CTL response and for improved methods of immunotherapy.

SUMMARY OF THE INVENTION

In one aspect, the invention provides a method for preparing a peptide antigen with modulated immunogenicity comprising substituting at least a first amino acid located in a CTL epitope with a first substitute amino acid having an extended or shortened side chain as compared to the first amino acid. The first substituted amino acid may have the same base (i.e. be a derivative or modification of the amino acid being substituted, such as having a derivatized or modified side chain) or a different residue as the first amino acid. The substituted amino acid may be a natural or non-natural amino acid. In certain embodiments of the invention, a modified side chain may be an aliphatic side chain. The first substitute amino acid may extend or shorten the side chain. In one embodiment of the invention, the first substitute amino acid adds 1, 2, 3, 4, 5 or more $—CH_2/CH_3$ groups to the side chain. In another embodiment of the invention, the first substitute amino acid shortens the side chain by 1, 2, 3 or more $—CH_2/CH_3$ groups on the side chain. A substitute amino acid may also eliminate an —OH group from the side chain. In still further embodiments of the invention, the first substitute amino acid eliminates or adds an $—NH_2$ group of a side chain. In certain aspects of the invention, the amino acid substitution increases the affinity of the antigen for a T cell receptor. In other embodiments of the invention, the substitution reduces interactions that interfere with T cell receptor binding.

In another aspect of the invention, the method for preparing a peptide antigen with modulated immunogenicity further comprises determining the CTL epitope of the antigen. In one embodiment of the invention, the method for preparing a peptide antigen comprises modeling a CTL epitope, including a CTL epitope bound in the MHC-I or MHC-II groove.

In still another aspect of the invention, the method for preparing a peptide antigen with modulated immunogenicity may comprise substituting at least a second amino acid located in the CTL epitope with a second substitute amino acid having an extended or shortened side chain as compared to the second amino acid. The method may also still further comprise substituting a third amino acid located in the CTL epitope with a third substitute amino acid having an extended or shortened side chain as compared to the third amino acid. In still further embodiments of the invention, the method may further comprise substituting a fourth amino acid located in the CTL epitope with a fourth substitute amino acid having an extended or shortened side chain as compared to the fourth amino acid.

The antigen may, in one embodiment of the invention, be a tumor antigen, including, for example, an antigen derived from breast cancer, ovarian cancer, prostate cancer, blood cancer, skin cancer, uterine cancer, cervical cancer, liver cancer, colon cancer, lung cancer brain cancer, head & neck cancer, stomach cancer, esophageal cancer, pancreatic cancer, or testicular cancer. In one embodiment of the invention, the tumor antigen is HER-2. In another embodiment of the invention, the antigen is a viral, bacterial or parasitic antigen.

In the method of preparing a peptide antigen with modulated immunogenicity, modulation of immunogenicity may comprise an increase in the antigen's ability to selectively activate high-avidity CTL precursors and/or low-avidity CTLs. Modulation of immunogenicity may still further comprise an increase in the antigen's ability to protect CTLs from activation induced cell death. Modulation may also comprise an increase in the antigen's ability to selectively activate cytokine production. In yet another embodiment of the invention, modulation of immunogenicity may comprise an increase in the antigen's ability to induce CTL proliferation.

In still yet another aspect, the invention provides a method of inducing immunity in a subject comprising administering to said subject a modified peptide antigen comprising a CTL epitope, wherein said antigen has at least one amino acid with a length-modified side chain, as compared to the same position in the natural molecule, within the CTL epitope. In the method, the subject may be an animal, including a human. The modified peptide antigen may be a modified tumor peptide antigen, and may also be a viral, bacterial or parasite antigen. The length-modified side chain may be extended or shortened as compared to the same position in the natural molecule. The modified peptide may further comprise a second amino acid with a length-modified side chain, as well as a third or fourth amino acid with a length-modified side chain. Each of these modified side chains may be shortened or lengthened as compared to the same position in the natural amino acid.

In still yet another aspect, the invention provides a method of treating a HER-2 related cancer comprising administering to said subject a modified E75 peptide, wherein said peptide has at least one amino acid with a length-modified side chain, as compared to the same position in the natural molecule. In the method, the HER-2 related cancer may be breast or ovarian cancer.

In still yet another aspect, the invention provides a peptide antigen with modulated immunogenicity prepared by substituting at least a first amino acid located in a CTL epitope with a first substitute amino acid having an extended or shortened side chain as compared to the first amino acid. Still further provided are vaccine compositions comprising the antigen as well as methods for therapeutically or prophylactically treating a patient for a tumor, viral, bacterial or parasitic disease comprising administering the vaccine to the patient.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1C. Induction or IFN-γ by A7.2, A7.3 and G4.3 in three healthy donors of PBMC (FIGS. 1A, 1B and 1C) Autologous MO-derived autologous DC were used as APC. Peptides were pulsed at 25 μg/ml exogenous concentration. IFN-γ was determined from the supernatant using specific ELISA.

FIGS. 2A-2B. (FIG. 2A) 7.2-primed T cells from Donor 1 respond to E7S with higher induction of IFN-γ "production rate". The x-axis intercept, tentatively indicate, the amount of A7.2 required to induce the same account of IFN-γ as E7S. (FIG. 2B) IL-2 production of $CH_2$-E7S primed T cells at restimulation with the same peptide.

FIGS. 3A-3C. (FIGS. 3A and 3B) Induction of higher CTL activity in CTL-TIL-1 at priming and restimulation with A7.3. S5.1+A7.2=specificity control immunogen made from A7.2 with Ser 5 replaced by homoserine (S5.1). (FIG. 3C) CTL-4 (E75 responding) after three stimulations with A7.0, A7.2, and A7.3, A7.3-induced CTL recognize E75 at 25 nM.

FIGS. 4A-4C. (FIGS. 4A and 4B) Priming with A7.2 followed by restimulation with A7.3 increase the numbers of hi-av E7S-specific CTL. (FIG. 4C) LU (E7s-specific) were determined from LU against T2-E7s minus LU against T2-NP. Rested "post effector" A7.3 induced CTL recognize E7s after restimulation with peptide.

FIGS. 5A-5D. CH2-E75 induced CTL recognize endogenously presented epitope. (FIG. 5A) CTL-3 was primed with E75 and restimulated with A7.2 and A7.3, respectively. (insert-IFN-γ and IL-2 responses to A7.0, A7.2 and A7.3 at priming). (FIG. 5B) Cold-target inhibition of lysis of SKOV3-A2 cells by CTL-3. A subpopulation of E75-specific cells recognize endogenously presented E75, with higher affinity based on 27% inhibition of lysis by T2-E75 (at 100 nM). (FIGS. 5C and 5D) CTL-TIL-HI recognition of SKOV3.A2 but not of SKOV3 is inhibited by T2-E75, confirming the specificity of these CTL.

FIGS. 6A-6C. Two color-FACS analysis of F8-1 (FIG. 6B), E75 (FIG. 6A), and positive control (FIG. 6C) influenza matrix-stimulated $CD8^+$ cells—Donor 1 after culture in IL-1. for 20 days. $CD61L^+$ CFSE (upper left quadrant, 1). $CD6L^+$ CFSE. cells (upper right quadrant, 2). F8-1 primed cells secreted higher levels of IFN-γ at restimulation with E75 (<200 pg/ml) E75 primed cells within 16 h (<75 pg/ml). In F8-1 cells, IFN-γ was also detected at 6 h.

FIGS. 7A-7B. (FIG. 7A) F42SK-CTL line were stimulated with agonistic αFas mAb (CH11) in the absence or presence of F42 or E75. Cell cycle analysis was performed 24 h and 96 h later in $CD8^+$ cells stained with propidium iodide (PI). Results indicate % apoptotic cells; i.e. cells in the sub $G_0$ phase. Exogenously pulsed F42 and E75 inhibited the residual Fas-apoptosis on day 1, but only E75 inhibited on day 4. (FIG. 7B) F42SK-CTL were restimulated with the indicated agonists pulsed on T2 cells. The sensitivity of F42-stimulated cells to αFas was paralleled by Bad up-regulation by F42 and lower Bcl-XL/Bad ratios than E75. (0 and NP) indicate either nonstimulated cells or cells stimulated with T2 with peptide. Equal numbers of cells were lysed, separated by SDS-PAGE, expression of Bcl-2, Bcl-XL and Bad determined with specific antibodies followed by Scanning Densitometry. Numbers indicate band intensity.

FIGS. 8A-8F Induction of effector functions in donor 1 (FIGS. 8A and 8B) and donor 2 (FIGS. 8C, 8D and 8E) at priming with the wild-type CTL epitope E75 and its variants. FIGS. 8A and 8C, IFN-γ; FIGS. 8B, 8D and 8E, Cytolysis. FIGS. 8A and 8C, IFN-γ was determined from supernatants collected from the same cultures which were used on day 8 for CTL assays. FIGS. 8B, 8D, and 8E, Equal numbers of effectors from each culture were tested in the same study. Results indicate the percentage of E75-specific lysis obtained by subtracting the specific lysis of T2 cells not pulsed with peptide, from the specific lysis of T2 cells pulsed with 25 μg/ml E75 in the same study. The E:T was 20:1. Stimulators were autologous DCs pulsed with 25 μg/ml peptide. NPs indicate control effectors that were stimulated only with autologous DCs which were not pulsed with peptide. FIG. 8E, Effectors E75-CTL, S5K-CTL, and S5A-CTL lysed the indicator ovarian tumor SKOV3.A2. Specific cold target inhibition indicated the percentage of inhibition of lysis of SKOV3.2 cells by cold (unlabeled) T2-E75 cells minus inhibition of lysis in the presence of T2-NP cells. S5G-CTL were not used here because their numbers declined rapidly after restimulation. E:T ratio was 30:1, cold:hot ratio was 10:1. FIG. 8F, Percentage of live cells in donor 2 cultures primed and restimulated with each variant 30 days after priming. Note the decrease in live cells in cultures stimulated with S5A or S5G. *, p<0.05.

FIGS. 9A-9C. FIG. 9A, Kinetics of IFN-γ production; FIG. 9B, E75-specific CTL induction; and FIG. 9C, survival of donor 3 CTL stimulated by E75 and S5K. Study details as described in Examples and the legend to the FIG. 8A, IFN-γ was determined on day 3 after stimulation with each peptide. The numbers 1, 2, and 3 indicate the number of stimulations. Equal numbers of live cells from E75- and S5K-stimulated cultures were stimulated with autologous DC pulsed with the corresponding peptide. FIG. 9C, The number of live cells recovered was determined 1 wk after the third and the fifth stimulations.

FIGS. 10A-10C. antigen specificity of S5A-CTL, S5K-CTL, and E75-CTL. FIG. 10A, Donor 1 S5A-CTL recognized S5K less efficiently than S5A. Donor 3 S5K-CTL recognized E75 with lower affinity than S5K. T2 cells were pulsed with E75 and S5K at 10 μg/ml. FIG. 10B, Donor 3 E75-CTL recognized S5K with lower affinity than E75. FIG. 10C, Donor 3 S5K-CTL recognized E75 with lower affinity than S5K-CTL. Concentration dependent recognition of E75 and S5K in the same study. Targets were T2 cells pulsed with the indicated concentrations of peptide. FIGS. 10B and 10C, Results of a 6-h CTL assay. E:T ratio was 10:1. *, p<0.05.

FIGS. 11A-11C. S5K-CTL recognized endogenous E75 presented by ovarian tumor cells. FIGS. 11A and 11B, Cold target inhibition of cytolysis of OVA-16 (HLA-A2, HER-$2^{high}$). Cold targets were T2 pulsed with E75, using as specificity control T2 which were not pulsed with peptide (T2-NP). Numbers in the parentheses indicate the percentage of inhibition of lysis of S5K-CTL by T2-E75 compared with lysis of tumor in the presence of T2-NP. *, p<0.05. E:T ratio was 10:1; the ratio of cold to hot targets was 1:1. C, IFN γ induction. IL-12 was used at 3 IU (300 pg/ml); the responders to SKOV3. A2 stimulator ratio was 40:1.

FIGS. 12A-12D. Expansion of CD8⁻ cells from S5K-CTL after stimulation with E75 (FIG. 12A) or S5K (FIG. 12B) in the absence (○) or presence (●) of CH11 mAb. Equal numbers of S5K-CTL were stimulated with DCs pulsed with 0, 25, and 50 μg/ml of each peptide. The number of CD8⁺ cells was determined by flow-cytometry using anti-CD8 mAb-FITC conjugated. FIG. 12C, antigen-induced resistance to CD95-mediated apoptosis. S5K-CTL were stimulated with autologous DCs pulsed with E75 or S5K at 5 and 25 μg/ml or control no peptide (0). CH11 mAb was added 1 h later. The number of apoptotic cells was determined 1 and 4 days later. FIG. 12D, Restimulation with E75 and S5K-induced resistance to CD95-mediated apoptosis in S5K-CTL stimulated 1 wk before with S5K. Apoptotic cells are shown in the panel subG1. Results are from one study representative of three independently performed studies. Bars indicate unstimulated (■), E75 stimulated (▨), E75+ anti-Fas stimulated (▦), S5K-stimulated (▨), and S5K⁻ anti-Fas stimulated (□).

FIGS. 13A-13D. FIG. 13A, Expression levels of Bcl-family members by S5K-CTL stimulated with the indicated peptides; or FIG. 13B, with PHA for 96 h. The same blot was used for probing with all Abs. 1 indicates unstimulated; 2 indicates PHA-stimulated cells. The numbers below the bands indicate the densitometric values (pixel total×10⁻³) FIGS. 13C and 13D, Expansion of E75⁺TCR cells in S5K-CTL stimulated in parallel with T2-E75 (E75), T2-S5K (S5K), or with T2-NP (NP) as control for 1 wk. The presence of E75⁺TCR cells was determined using dE75 (y-axis). Forward scatter (FW) is shown on x-axis. FIG. 13C, E75⁺ TCR cells expression in large lymphocytes (FW: 640-1000); FIG. 13D, E75⁺TCR expression on small lymphocytes (FW: 380-600). The percentage of dNP⁺ cells ranged from 0.1-0.5% in both populations.

FIGS. 14A-14D. Stimulation of S5K-CTL with E75 significantly increased the number of E75⁺TCR cells. FIG. 14A, Percentage of E75⁺TCR cells in the large (▨) and small (▨) lymphocytes was determined immediately after staining and 50 min after washing and incubation of cells in PBS to dissociate low-affinity ($t_{1/2}$<50 min) TCR-dE75 complexes. Most small lymphocytes recognized E75 with $t_{1/2}$ of <50 min, while ~50% of large lymphocytes had a $t_{1/2}$ of 50 min for E75. FIG. 14B, Increase in the numbers of E75⁺TCR cells of S5K-CTL after stimulation with E75 and S5K large (▨) and small (▨) lymphocytes. The numbers of live cells recovered after stimulation with T2-NP, T2-E75, and T2-S5K, and expansion in IL-2 were 2.7, 3.2, and 2.9×10⁶ cells, respectively. FIG. 14C, Increased levels of expression of E75⁺TCR in large lymphocytes stimulated with E75 compared with S5K. The differences in MCF in small lymphocytes were minimal: 202 for E75, 180 for S5K. FIG. 14D, Increased levels of expression of Bcl-2 in E75⁺ TCR large lymphocytes but not in small lymphocytes at stimulation with E75 or S5K. All determinations were performed in the same study. Results are from one determination representative of two with similar results.

DESCRIPTION OF ILLUSTRATIVE EMBODIMENTS

The invention overcomes the limitations of the prior art by providing methods for the modulation of TCR signaling using modified antigens, thereby providing each of the required steps for developing successful immunological therapies, including cancer therapies. For example, this can be accomplished in accordance with the invention by introducing discrete changes in the aliphatic side chain length of the same residue, at the same position in the stimulating antigen (Ag). This can comprise the addition or removal of $CH_2$ (methylene) groups from the side chain. $CH_2$ groups are smaller than OH and $NH_2$ groups and do not form electrostatic or H-bonds, but do form weaker hydrophobic van der Waals bonds which increase in proportion to the number of $CH_2$ added. These bonds should also modulate the avidity (or half-life) of peptide for TCR, which is a requirement for transformation of an antigen into a stronger or a weaker agonist. HAB antigen can also modulate survival and avoid inducing apoptosis by over-stimulation by decreasing the number of $CH_2$ groups. T cell development studies have shown that TCR modifies its response to antigen side chain changes even at the level of one $CH_2$ group.

By extension or shortening of the side chain with $CH_3$/ $CH_2$ groups, for example, done by computer assisted modeling of the tumor antigen (peptide) bound in the MHC-I groove, immunogenicity can be improved with minimal modification of adjacent tertiary structure, thereby avoiding cross-reactivity. Detection of T cell activation by this novel method allows modification of the stimulating intensity of the tumor antigen by $CH_2$ deletion or addition, allowing circumvention of induction of apoptosis by under/over-stimulation of lymphocytes.

The invention thus, in one aspect, provides methods of activation of immunity to a tumor or pathogen as follows: (1) the methods may be used for selective activation of high-avidity precursors of tumor/pathogen reactive CTL using an attenuated antigen from the tumor or pathogen comprising shortened $CH_2$ side chains (type 1 agonists); (2) activation of low-avidity CTL against the tumor/pathogen using $CH_2$ side chain extended antigen ("amplifying agonists") (type 2 agonists); (3) protection from activation induced cell death (AICD) by re-stimulation of cells previously activated with type 2 agonists above with even more attenuated agonists (type 3) than the ones listed in type 1; (4) selective activation of cytokine production or of both cytokine production and proliferation by the manipulation of the CH2 side chain length at two distinct positions; (5) ability to target the positions where the changes will be made using molecular modeling of the tumor/pathogen antigen MHC-I, as well as tumor/pathogen antigen-MHC-II complex; (6) applicability to most if not all tumor or pathogen antigen. The poor immunogenicity of tumor and some other antigen may not be due only to the low affinity of the antigen for the TCR but also to interference of side chains with interactions by other side chains with TCR. Therefore, the invention may be used to overcome these limitations.

Vaccine therapies raise the need for hi-av CTL for the peptide-MHC complex presented by the target antigen. Induction of hi-av CTL using "heteroclitic antigen" requires replacement of core residues in the peptide. While this approach was found to enhance responses to some antigen, for others the resulting CTL were of lower affinity for a target tumor than wild-type CTL. Excess signaling by heteroclitic antigen and partial signaling by wild type antigen could specifically eliminate both antigen-specific and cross-reactive CTL in vivo, and this elimination extends to bystander T-cells.

There were previously no approaches for modulation of TCR signaling of hi-av CTL for protection from apoptosis, survival, and progression to memory. This is important because: (a) TCR signals at re-stimulation with the initiating antigen enhance the susceptibility to Fas-mediated apoptosis, while IL-2 amplifies the death inducing effects of Fas; (b) cessation of antigen stimulation and withdrawal of growth factors also lead to death of effectors; (c) extensive proliferation rapidly leads to generation of end-stage of differentiated CTL, which die via apoptosis even before disease recurrence. This shortens the life-span of mCTL; (d) whether optimal generation of mCTL requires them to revert to a resting $G_0/G_1$ phenotype and to proliferate slowly and intermittently in response to antigen or continuously in response to cytokines has not yet been elucidated; (e) the dependence of cell survival on MAPK (ERK) controlled pathways raise the need for intermittent antigen signaling (as an alternative) when cytokines (IL-15) are absent or are below the levels that can activate survival pathways.

Thus, the concept for vaccination by changing TCR signaling in a subtle manner to direct the progression of CTL through the desired steps entails the use of three immunogens targeting the same CTL, but each acting at a defined step and endowed with the ability to expand precursors, activate and expand eCTL, and protect mCTL, respectively. HAB antigen maintain the core residues of the wild type antigen with their charged and —OH groups, thus the position and orientation in the binding pocket is unchanged.

I. MODIFIED ANTIGENS

Identification and modification of tumor or pathogen antigens which are the target of CTL allows vaccination for therapeutic or prophylactic benefit. A number of antigen, and in particular, the majority of tumor antigen, are weak partial agonists, which induce low levels of cytolysis by low-avidity CTL. Little is known about the strategies that may render success in using tumor or pathogen antigens for vaccination of a subject. The outcome of TCR activation is dependent on the affinity of TCR for the peptide-MHC. Extended TCR stimulation may activate TCR-negative feedback pathways. The current invention can be used to avoid such problems.

In accordance with the invention, however, induction of high-avidity CTL can be carried out by modulation of TCR signaling using modified antigen of focused specificity and increased capability for van der Waals forces. Initial studies to demonstrate the effectiveness of the approach were carried out using molecular modeling of the HER-2 peptide E75-HLA-A2 complex and identification of $CH_2$ side chains pointing upwards and sideways. E75 is recognized frequently by tumor reacting ovarian and breast CTL-TIL, as well as by CTL from transgenic models. Phase I clinical studies, show that E75 lacks toxicity, but induce immune responses being presented by the tumor.

Modifications of the length of side-chains were made in Gly4, Ala7, and Phe8 by replacement with NVal, NLeu and HomoPhe(-$CH_2$), respectively and Ser5 by replacement with Gly. The corresponding immunogens were designated as G4.3, A7.2, A7.3 8.-1, and S5.-1, respectively. Of these, A7.2 induced higher levels of IFN-γ than A7.3 and G4.3 in cells from donors and ovarian cancer patients which did not respond to E75, indicating increased signaling by a $CH_2$ extension. Further, A7.2-primed cells responded to E75 faster with higher levels of IFN-γ, than E75-primed cells. E75-specific CTL were induced by A7.2 and A7.3.

A. Design of $CH_2$-Modified Immunogens

The HER-2 peptide E75 (369-377) has been identified as an immunodominant epitope recognized by ovarian tumor reactive CTL (Fisk et al., 1995; Rongcun et al., 1999; zum Buschenfelde et al., 2000). This raises the possibility of using E75 or of fragments of HER-2 containing this epitope for cancer vaccination. E75 induced IFN-γ even in unfractionated PBMC in the majority of healthy donors or E75 vaccinated patients (Lee et al., 2000; Zaks and Rosenberg, 1998; Anderson et al., 2000). E75-induced CTL also recognized HLA-A2[1] HER-2[1] tumors by secretion of IFN-γ. These effects could be augmented by addition of low levels (100 pg/ml) of IL-12 (Anderson et al., 2000).

E75 is a weak inducer of cytolytic activity against tumor cells (Zaks and Rosenberg, 1998; Anderson et al., 2000). The cytolytic activity of E75 (peptide)-induced CTL was significantly weaker against tumor cells expressing HER-2. Endogenously, E75 is presented by tumor cells, indicating that E75 is an important immunogen for induction of anti-tumor activity (zum Buschenfelde et al., 2000; Fisk et al., 1997). E75 is a weak partial agonist of which the ability to induce lytic effector does not improve by the use of DC as APC, IL-2, IL-12, TNF-α or of various pretreatments (IL-2, RANTES) of responders (Lee et al., 2000; Anderson et al., 2000). This demonstrated the need for optimization of immunogenicity of E75, to induce eCTL, and to enhance survival of mCTL.

B. Modeling of CTL Epitope-MHC Complexes

One aspect of the invention comprises identifying a CTL epitope and discerning the secondary structure of the complex between CTL epitopes and class I and/or class II MHC molecules. With this information, side chains involved in the interaction with the T-cell receptor can be modified as described herein. Numerous scientific publications have been devoted to the prediction of secondary structure of a given epitope or molecule and may be used in accordance with the invention (see, e.g., Chou and Fasman, 1974a,b; 1978a,b, 1979). Moreover, computer programs are currently available to assist with predicting an antigenic portion and an epitopic core region of one or more proteins, polypeptides or peptides. Examples include those programs based upon the Jameson-Wolf analysis (Jameson and Wolf, 1988; Wolf et al., 1988), the program PepPlot® (Brutlag et al., 1990; Weinberger et al., 1985), and other programs for protein tertiary structure prediction (Fetrow and Bryant, 1993). Another commercially available software program capable of carrying out such analyses is MacVector (IBI, New Haven, Conn.). In addition to the computer programs commercially available for analysis of protein-protein interactions, Simon et al. (2002), for example, described a program optimized for analysis of MHC class II molecules complexed with various peptides fitting into the MHC class II groove.

To determine whether a modification to an epitope will affect the interaction with a TCR, the putative location of the modified amino acid(s) could be determined by comparison of the mutated sequence to that of the unmutated polypeptide's secondary and tertiary structure, as determined by such methods known to those of ordinary skill in the art including, but not limited to, X-ray crystallography, NMR or computer modeling. X-ray crystallography in particular has proved useful for the determination of the structure of antigen-MHC complexes. For example, the elucidation of the structure of different peptide complexes between an antigen and MHC molecules by X-ray crystallography was described by, e.g., Madden (1995) and Stern and Wily (1994). X-ray crystallography has also been used to elucidate the structure of a viral peptide-HLA-A2 complex bound in the human TCR (Garboci et al., 1996).

In further embodiments of the invention, major CTL epitopes of a polypeptide antigen may be identified by an empirical approach in which portions of the gene encoding the polypeptide are expressed in a recombinant host, and/or the resulting proteins tested for their ability to elicit an immune response. For example, PCR™ can be used to prepare a range of peptides lacking successively longer fragments of the C-terminus of the protein. The immunoactivity of each of these peptides is determined to identify those fragments and/or domains of the polypeptide that are immunodominant. Further studies in which only a small number of amino acids are removed at each iteration then allows the location of the antigenic determinants of the polypeptide to be more precisely determined.

Once one and/or more such analyses are completed, epitopes may be modified as is described herein. The peptides may then be employed in the methods of the invention to modulate an immune response as is desired by administration of an antigen bearing the epitope to a mammal, preferably a human.

C. Cytotoxic T Lymphocytes

T lymphocytes arise from hematopoietic stem cells in the bone marrow, and migrate to the thymus gland to mature. T cells express a unique antigen binding receptor on their membrane (T-cell receptor), which can only recognize antigen in association with major histocompatibility complex (MHC) molecules on the surface of other cells. There are at least two populations of T cells, known as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a T cytotoxic cells that recognizes an antigen-MHC complex proliferates and differentiates into an effector cell called a cytotoxic T lymphocyte (CTL). CTLs eliminate cells of the body displaying antigen, such as virus infected cells and tumor cells, by producing substances that result in cell lysis.

The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is refereed to as the HLA complex and in mice the H-2 complex.

In certain embodiments of the invention, T-lymphocytes are specifically activated by contact with an antigenic composition comprising a modified CTL epitope. In one embodiment of the invention, this could comprise activating T-lymphocytes by contact with an antigen presenting cell that is in contact with an antigen of the invention. T cells express a unique antigen binding receptor on their membrane, a T-cell receptor (TCR), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a T cytotoxic cell that recognizes an antigen-MHC complex proliferates and differentiates into an effector cell called a cytotoxic T lymphocyte (CTL). CTLs eliminate cells of the body displaying antigen, such as virus infected cells and tumor cells, by producing substances that result in cell lysis.

II. MODIFIED CTL EPITOPES

Optimization of immunogenicity requires approaches for controlled modulation of TCR (T-cell antigen receptor)

signaling by antigen (antigen). Studies on positive selection, survival, as well as induction of memory CTL (mCTL), indicate the requirement for modulation of TCR signaling to allow progression of T cells from naive to effector CTL (eCTL) and memory CTL (mCTL) (Williams et al., 1999; Roy and Nicholson, 2000; Krammer, 2000). Attenuation of the strength of TCR signaling should thus be able to avoid AICD-mediated death by overstimulation, as well as induce homeostatic proliferation of precursors of hi-av T cells which should be more sensitive to low affinity ligands.

The approach of the inventors thus provides methods for modulation of TCR signaling. By addition of $CH_2$-groups in the side chains of the amino acids of a target antigen in positions pointing upwards and sideways, this will allow increased affinity of the peptide for the TCR because of increased availability of $CH_2$— groups to form van der Waals interactions with TCR. Because the maintenance of the peptide core, and of charged polar, or phenol rings in place, these antigen will be less cross-reactive with other TCR than CTL induced by enhancer agonists. Thus, modulation of TCR signaling will not require amino acid substitution in the core with unpredicted effects due to modification of positions of core residues in the groove, and modification of the surfaces presented to TCR. The increase/decrease in the available $CH_2$ groups should modify the half-life and the affinity (Kd) of the TCR for the peptide. Thus, modification of $CH_2$ side chain length at defined positions allows modulation of TCR signaling, according to the requirements for overt or attenuated stimulation of cells in various stages of differentiation.

It is thus indicated that if new interactions created by $CH_2$ addition are functional, they will either increase the affinity for TCR or will disrupt existent nonproductive interactions. Thus, corresponding analogs should be more immunogenic than the Wild type agonists, for activation of same effector function. If $CH_2$ extension is done in residues with short or absent side chains (Ala, Gly) which do not point upward, the interference with existent interactions by other side chains will be minimized. Thus, the objectives of the studies described below were to determine the immunogenicity of $CH_2$-E75 analogs.

Since it is the interactive capacity and nature of an antigen that defines its biological (e.g., immunological) functional activity, certain amino acid sequence substitutions should be made with consideration to the structure of the amino acid substituted. As used herein, an "amino molecule" refers to any amino acid, whether natural or non-natural, including amino acid derivatives or amino acid mimics as would be known to one of ordinary skill in the art. In certain embodiments, the residues of the antigenic composition comprise amino molecules that are sequential, without any non-amino molecule interrupting the sequence of amino molecule residues. In other embodiments, the sequence may comprise one or more non-amino molecule moieties. In particular embodiments, the sequence of residues of the antigenic composition may be interrupted by one or more non-amino molecule moieties. In certain other embodiment of the invention, non-natural amino acids are used to replace natural amino acids in a native CTL epitope. Accordingly, antigenic compositions prepared in accordance with the invention may encompass an amino molecule sequence comprising at least one of the 20 common amino acids in naturally synthesized proteins, as well as at least one modified or unusual amino acid, including but not limited to those shown in Tables 1 and 2 below.

In substituting amino acids, it may also be desired to consider the relative hydrophobicity, hydrophilicity, charge, size, and/or the like of the amino acids. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape.

Antigenic epitope-bearing peptides and polypeptides of the invention designed according the guidelines described herein generally will preferably contain a sequence of at least seven to about 15 to about 30 amino acids contained within the amino acid sequence of a polypeptide of the invention. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

In terms of immunologically functional equivalents, it is well understood by the skilled artisan that there is a limit to the number of changes that may be made within a defined portion of a molecule and still result in a molecule with an acceptable level of equivalent immunological activity. An immunologically functional equivalent peptide or polypeptide are thus defined herein as those peptide(s) or polypeptide(s) in which certain, typically not most or all, of the amino acid(s) may be substituted. In particular, where a shorter length peptide is concerned, it is contemplated that fewer amino acid substitutions should be made within the given peptide. A longer polypeptide may have an intermediate number of changes. The full length protein will have the most tolerance for a larger number of changes. Of course, a plurality of distinct polypeptides/peptides with different substitutions may easily be made and used in accordance with the invention.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,833,092 to Geysen (1989) describes a method of detecting or determining a sequence of monomers which is a topographical equivalent of a ligand which is complementary to the ligand binding site of a particular receptor of interest.

Similarly, U.S. Pat. No. 5,480,971 to Houghten, et al. (1996) on Peralkylated Oligopeptide Mixtures discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

It also is well understood that where certain residues are shown to be particularly important to the immunological or structural properties of a protein or peptide, e.g., residues in binding regions or active sites, such residues may not generally be exchanged absent the side-chain changes described herein. In this manner, functional equivalents are defined herein as those peptides or polypeptides which maintain a substantial amount of their native immunological activity or possess increased immunological activity.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein, polypeptide or peptide is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity, particularly where the immunological functional equivalent polypeptide or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a immunological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. Nucleic acids encoding these antigenic compositions also can be constructed and inserted into one or more expression vectors by standard methods (Sambrook et al., 2001), for example, using PCR™ cloning methodology.

Certain aspects of the instant invention comprise synthesis of peptide and polypeptide epitopes in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. As described herein, these amino acids may in particular find use in the creation of modified CTL epitopes. A table of exemplary, but not limiting, modified and/or unusual amino acids is provided herein below in Table 1.

TABLE 1

Modified and/or Unusual Amino Acids

| Abbr. | Amino Acid |
|---|---|
| Aad | 2-Aminoadipic acid |
| BAad | 3-Aminoadipic acid |
| BAla | Beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In making amino acid substitutions in accordance with the invention, it will be desired to particularly consider side-chain modifications. Non-limiting examples of specific side-chain modifications contemplated for use with the current invention, including specific side chain lengthening or shortening modifications, are set forth below in Table 2:

TABLE 2

Exemplary Amino Acid Substitutions for Linear Lengthening or Shortening of Side Chains with Un-Natural Amino Acids

| Analogs of Ala7: (Ala7: R chain = $CH_3$) | |
|---|---|
| Compound | Reagent Used with side chain amino acid longer than Natural Glycine ($CH_2$=O) |
| R chain = $CH_2CH_3$ | -aminobutyric acid (+1 $CH_2$) Fmoc-Abu-OH N-α-fmoc-L-α-aminobutyric acid Fmac-2-aminobutanaic acid $C_{19}H_{19}NO_4$; M.W.: 325-4 |
| R chain = $Ch_2CH_2CH_3$ | Norvaline (+2 $CH_2$) Fmoc-Nle-OH N-α-fmac-L-norvaline $C_{20}H_{21}NO_4$; M.W.: 339.4 |
| R chain = $CH_2CH_2CH_2CH_3$ | Norleucine (+3 $CH_2$) Fmoc-Nle-OH N-α-fmac-L-norleucine CAS No. 77284 32-3; $C_{21}H_{23}NO_4$; M.W.: 353.4 |
| Analogs of Phe8 (Phe8: R chain = $Ch_2(C_6H_5)$) | |
| Compound | Reagent Used |
| R chain = $C_6H_5$ | Phenyl Glycine (−1$CH_2$) Fmac-Phg-OH N-α-fmac-L-phenylglycine $C_{23}H_{19}NO_4$; M.W.: 373.4 |

TABLE 2-continued

Exemplary Amino Acid Substitutions for Linear Lengthening or Shortening of Side Chains with Un-Natural Amino Acids Analogs of Lys1 (R chain = CH₂CH₂CH₂CH₂NH₂)

| Compound | Reagent |
|---|---|
| R chain = Ch₂CH₂CH₂NH₂ | Ornithine (—CH₂)<br>Fmac-Orn(Bac)-OH<br>N-α-Fmac-N-6-Bac-L-ornithine<br>CAS No: 109425-55-0;<br>C₂₅H₃₀N₂O₆; M.W.: 454.5 |
| R chain = CH₂CH₂CH₂CH₂CH₂NH₂ | Homolysine (+1 CH₂) |
| 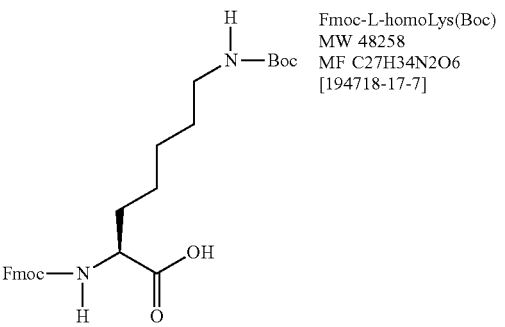 | Fmoc-L-homoLys(Boc)<br>MW 48258<br>MF C27H34N2O6<br>[194718-17-7] |

Analogs of Ile2: (R chain = (CH(CH₃)CH₂CH₃)*

| Compound | Reagent |
|---|---|
| R chain: CH₂CH(CH₃)CH₂CH₃ | γ-Methyl 1-leucine(+1 CH₂)<br>H-Leu(γMe)-OH<br>γ-Methyl-L-leucine<br>C₇H₁₅NO₂; M.W.: 145.2 |

Analogs of Phe3: (R chain = Ch₂(C₆H₅))

| Compound | Reagent Used |
|---|---|
| R chain = C₆H₅ | Phenyl Glycine (−1CH₂)<br>Fmac-Phg-OH<br>N-α-fmac-L-phenylglycine<br>C₂₃H₁₉NO₄; M.W.: 373.4 |
| R chain: CH₂CH₂(C₆H₅) | Homophenylalaine (+1 CH₂) |
| 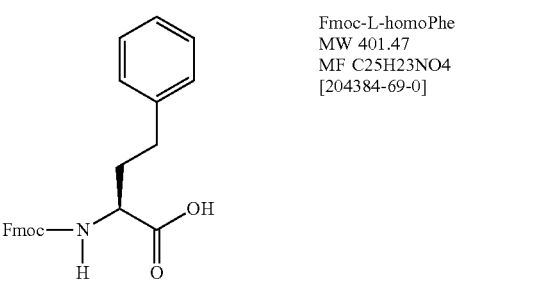 | Fmoc-L-homoPhe<br>MW 401.47<br>MF C25H23NO4<br>[204384-69-0] |

Gly4: (R chain = H)**

CH₂-Analogs of Ser 5 (R chain = CH₂OH)

| Compound | Reagent |
|---|---|
| R chain: OH | 2-amino 2-hydroxy Acetic Acid (−1 CH₂) (unstable under peptide synthesis conditions) |
| R chain: CH₂CH₂OH | Homoserine (+1 CH₂)<br>Fmoc-Hse(Trt)-OH<br>N-α-fmac-O-trityl-L-homoserine<br>C₃₈H₃₃NO₅; M.W.: 583.7 |

TABLE 2-continued

Exemplary Amino Acid Substitutions for Linear Lengthening or Shortening of Side Chains with Un-Natural Amino Acids Analogs of Leu6 (R Chain = CH₂CH(CH₃)₂***

| Compound | Reagent |
|---|---|
| R chain: CH₂CH₂CH(CH₃)₂ | Homoleucine (+1 CH₂) |
| Ala7: R Chain-CH₃ | Previously tested |
| See Phe3 | |
| See Leu6 | |

*Since the first carbon of the R chain is branched, eliminating this carbon to form a (−1 CH) structure would radically affect the makeup of this amino acid and may cause unwarranted side reactions.
**Any alterations in the side chain of this amino acid results in a non-homologous amino acid.
***Removing the first methylene group to make a (−1 CH₂) compound results in the formation of the natural amino acid Valine.

A. Epitopic Core Sequences

One aspect of the current invention provides for the modification of peptide epitope-bearing portions of an antigen in order to modulate TCR signaling and to achieve a therapeutic benefit therefrom. The epitope of this antigen can be termed an immunogenic or antigenic epitope. An "immunogenic epitope" is defined as a part of a antigen that interacts with MHC class I and/or class II molecules and/or the TCR, eliciting a TCR-mediated response to the antigen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, (1984).

Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., 1984. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

B. Identifying CTL Epitopes

Numerous techniques for the identification of CTL epitopes are known to those of skill in the art and may be employed in connection with the instant invention. For example, various computer-based prediction algorithms have been described and are publicly available to identify tumor-reactive CTL epitopes (see, e.g., Lu and Celis, 2000). For example, Falk et al. (1991) describe a method for prediction of HLA A2.1 haplotypes by computer software. A common strategy in the search for epitope containing antigens is to first isolate T-cells specific for the antigen and attempt to identify the antigen(s) recognized by the T-cells. For example, in patients with cancer, specific CTLs have been often derived from lymphocytic infiltrates present at the tumor site (Weidmann et al., 1994). Tumor-specific CTLs have also been found in peripheral blood or malignant ascites of patients with cancer, indicating that a systemic response to the tumor may be present or that redistribution of CTLs from the tumor to the periphery might occur (Wallace et al., 1993).

Common protocols for CTL epitope identification involve isolating and assaying extremely pure MHC molecules from antigen-presenting cells. Prior to peptide extraction, all contaminating proteinaceous material must be removed (Chicz and Urban, 1994). Using immunoaffinity purification, bound HLA molecules are obtained. From these, smaller amounts of bound peptide can be isolated and further purified, such as by HPLC. These fractions can be assayed for reactivity with cloned CTLs and can be sequenced or otherwise characterized.

In another technique, developed by Van der Zee et al. (1989) and referred to as the "pepscan" technique, dozens of peptides are simultaneously synthesized on polyethylene rods arrayed in a 96-well microtiter plate pattern. Peptides are then chemically cleaved from the solid support and supplied to irradiated syngeneic thymocytes for antigen presentation. A cloned CTL line is then tested for reactivity in a proliferation assay monitored by $^3$H-thymidine incorporation. This type of analysis particularly suits a CTL stimulation assay since it can be automated using a microtiter plate reader and employs relatively low levels of radiation. The technique is highly specific.

Yet another method for identification of CTL epitopes is described in U.S. Pat. No. 6,338,945, the entire disclosure of which is specifically incorporated herein by reference. In this technique, CTL epitopes are identified by screening solid phase combinatorial libraries of molecules in a cytotoxic T cell assay. In this way, CTLs activated by the molecules in the library are identified.

T cell epitopes may also be predicted utilizing the HLA A2.1 motif described by Falk et al. (1991). From this analysis, peptides may be synthesized and used as targets in an in vitro cytotoxic assay. Still another method that may also be utilized to predict immunogenic portions is to determine which portion has the property of CTL induction in mice utilizing retroviral vectors (see, Warner et al., 1991). As noted in Warner et al., CTL induction in mice may be utilized to predict cellular immunogenicity in humans. Preferred immunogenic portions may also be deduced by determining which fragments of an antigen are capable of inducing lysis by autologous patient lymphocytes of target cells (e.g., autologous EBV-transformed lymphocytes) expressing the fragments after vector transduction of the corresponding genes.

U.S. Pat. No. 4,554,101, (Hopp) incorporated herein by reference, teaches the identification and/or preparation of epitopes from primary amino acid sequences on the basis of hydrophilicity. Through the methods disclosed in Hopp, one of skill in the art would be able to identify epitopes from within an amino acid sequence.

C. Production of Modified Antigens

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized (by ELISA-type binding studies) in less than four weeks, Houghten, (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously. Houghten et al., supra, at 5134.

Immunogenic TCL epitope-bearing peptides of the invention, i.e., those parts of a antigen that interact with MHC molecules and/or TCR, may be prepared according to methods known in the art. For instance, Geysen et al., 1984, supra, discloses a procedure for rapid concurrent synthesis on solid supports of hundreds of peptides of sufficient purity to react in an enzyme-linked immunosorbent assay. Modulation of immunogenicity can then be easily assayed as described herein below. In this manner a peptide bearing a modified immunomodulatory CTL epitope may be identified routinely by one of ordinary skill in the art.

For instance, combining synthetic preparation of the immunologically important epitope in the coat protein of foot-and-mouth disease virus combined with assays for immunologic activity, Geysen et al. identified the epitope with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made by this method. U.S. Pat. No. 4,708,871 to Geysen (1987) further describes this method of identifying a peptide bearing an immunogenic epitope of a desired protein.

III. TREATMENT OR PREVENTION OF DISEASE WITH THE INVENTION

The disclosures presented herein have significant relevance to immunotherapy of human diseases and disorders including, but not limited to, cancer. In using the immunotherapeutic compositions and methods of the present invention in treatment methods, other standard treatments also may be employed, such as radiotherapy or chemotherapy. However, in certain instances it may be preferred to use the immunotherapy alone initially so that its effectiveness can be readily assessed. Certain aspects of the invention thus concern methods for the prevention or treatment of disease. Such disease may be external in origin, for example, in the case of infection by bacterial, viral, parasitic or other types of causative agents. The disease may also be internal in origin, for example, in the case of spontaneous carcinogenesis.

A. Vaccine Preparations

A modified antigenic composition of the present invention may be mixed with one or more additional components (e.g., excipients, salts, etc.) which are pharmaceutically acceptable and compatible with at least one active ingredient (e.g., antigen) to form a composition suitable for administration to an animal, for example, a human. Such a composition may be termed a "vaccine". As used herein, the term "vaccine" refers to any composition formulated for administration to an animal, including a human, and which includes one or more antigen(s) prepared in accordance with the invention, whether used or intended to be used for prophylactic administration to prevent development of disease and/or for therapeutic administration for mitigation or elimination of an existing disease state. The preparation of such vaccines is generally well understood in the art, as exemplified by U.S. Pat. Nos. 4,608,251, 4,601,903, 4,599,231, 4,599,230, and 4,596,792, all incorporated herein by reference. These methods may therefore be used to prepare a vaccine comprising an antigenic composition comprising one or more epitopes modified as described herein as an active ingredient. In preferred embodiments, the compositions of the present invention are prepared to be pharmacologically acceptable vaccines.

Pharmaceutical vaccine compositions of the present invention comprise an effective amount of one or more modified antigens and any desired additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one antigen prepared in accordance with the invention or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The composition may comprise different types of carriers depending on whether it is to be administered in solid, liquid or aerosol form, and whether it need to be sterile for such routes of administration as injection. Except insofar as any conventional carrier is incompatible with the active ingredient, its use in the therapeutic or pharmaceutical compositions is contemplated.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compositions may be formulated in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc., lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments of the invention, the antigen may be prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

For an antigenic composition to be useful as a vaccine, an antigenic composition must induce an immune response to the antigen in a cell, tissue or animal (e.g., a human). As used herein, an "antigenic composition" refers to a composition comprising one or more antigens comprising at least a first epitope modified as described herein. In other embodiments, the antigenic composition is in a mixture that comprises an additional immunostimulatory agent or nucleic acids encoding such an agent. Immunostimulatory agents include but are not limited to an additional antigen, an immunomodulator and an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In certain embodiments of the invention, an antigenic composition or immunologically functional equivalent, may be used as an effective vaccine in modulating a humoral and/or cell-mediated immune response in an animal. Such modulation may, for example, be used for the treatment or prevention of cancer or of a disease caused by an infective agent as described herein. One or more antigenic compositions or vaccines may be used in both active and passive immunization embodiments. In a non-limiting example, a nucleic acid encoding an antigen might also be formulated with a proteinaceous adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure. One of skill in the art may wish to add one or more components to such a vaccine in addition to an antigen of the invention, including, but not limited to the agents discussed below.

B. Additional Vaccine Components

1. Immunomodulators

It is contemplated that immunomodulators can be included in a vaccine to augment a cell's or a patient's (e.g., an animal's) response. Immunomodulators can be included as purified proteins, nucleic acids encoding immunomodulators, and/or cells that express immunomodulators in the vaccine composition. The following sections list non-limiting examples of immunomodulators that are of interest, and it is contemplated that various combinations of immunomodulators may be used in certain embodiments (e.g., a cytokine and a chemokine).

a. Cytokines

Interleukins, cytokines, nucleic acids encoding interleukins or cytokines, and/or cells expressing such compounds are contemplated as possible vaccine components. Interleukins and cytokines, include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH-1, METH-2, tumor necrosis factor, TGFβ, LT and combinations thereof.

b. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

c. Immunogenic Carrier Proteins

In certain embodiments, an antigenic composition of the invention may be chemically coupled to a carrier or recombinantly expressed with a immunogenic carrier peptide or polypeptide (e.g., a antigen-carrier fusion peptide or polypeptide) to enhance an immune reaction. Exemplary immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m-maleimidobenzoyl-N-hydroxy-succinimide ester, carbodiimide and bis-biazotized benzidine.

d. Biological Response Modifiers

It may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m$^2$) (Johnson/Mead, NJ), or a gene encoding a protein involved in one or more immune helper functions, such as B-7.

2. Adjuvants

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

In one aspect, an adjuvant effect is achieved by use of an agent, such as alum, used in about 0.05 to about 0.1% solution in phosphate buffered saline. Alternatively, the antigen is made as an admixture with synthetic polymers of sugars (Carbopol®) used as an about 0.25% solution. Adjuvant effect may also be made by aggregation of the antigen in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cell(s) such as *C. parvum*, an endotoxin or a lipopolysaccharide component of Gram-negative bacteria, emulsion in physiologically acceptable oil vehicles, such as mannide mono-oleate (Aracel A), or emulsion with a 20% solution of a perfluorocarbon (Fluosol-DA®) used as a block substitute, also may be employed.

Some adjuvants, for example, certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

Adjuvants have been used experimentally to promote a generalized increase in immunity against unknown antigens (e.g., U.S. Pat. No. 4,877,611). This has been attempted particularly in the treatment of cancer. For many cancers, there is compelling evidence that the immune system participates in host defense against the tumor cells. The current invention provides for such treatments by providing improved antigen compounds.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin. Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is the to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

Another adjuvant contemplated for use in the present invention is BCG. BCG (*bacillus* Calmette-Guerin, an attenuated strain of *Mycobacterium*) and BCG-cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945.

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present invention.

One group of adjuvants preferred for use in the invention are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

In other embodiments, the present invention contemplates that a variety of adjuvants may be employed in the membranes of cells, resulting in an improved immunogenic composition. The only requirement is, generally, that the adjuvant be capable of incorporation into, physical association with, or conjugation to, the cell membrane of the cell in question. Those of skill in the art will know the different kinds of adjuvants that can be conjugated to cellular vaccines in accordance with this invention and these include alkyl lysophosphilipids (ALP); BCG; and biotin (including biotinylated derivatives) among others. Certain adjuvants particularly contemplated for use are the teichoic acids from Gram negative cells. These include the lipoteichoic acids (LTA), ribitol teichoic acids (RTA) and glycerol teichoic acid (GTA). Active forms of their synthetic counterparts may also be employed in connection with the invention (Takada et al., 1995).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

One group of adjuvants preferred for use in some embodiments of the present invention are those that can be encoded by a nucleic acid (e.g., DNA or RNA). It is contemplated that such adjuvants may be encoded in a nucleic acid (e.g., an expression vector) encoding the antigen, or in a separate vector or other construct. These nucleic acids encoding the adjuvants can be delivered directly, such as for example with lipids or liposomes.

C. Preparation of Proteinaceous Antigens

It is understood that an antigenic composition of the present invention may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an antigen of the present invention in an in vitro translation system or in a living cell. Preferably the antigenic composition is isolated and extensively dialyzed to remove one or more undesired small molecular weight molecules and/or lyophilized for more ready formulation into a desired vehicle. It is further understood that additional amino acids, mutations, chemical modification and such like, if any, that are made in a vaccine component will preferably not substantially interfere with recognition of the epitopic sequence.

A peptide antigen modified in accordance with the invention may be synthesized by methods known to those of ordinary skill in the art, such as, for example, peptide synthesis using automated peptide synthesis machines, such as those available from Applied Biosystems (Foster City, Calif.). Longer peptides or polypeptides also may be prepared, e.g., by recombinant means. Polypeptides produced by these or other techniques may be modified by substitution or modification of one or more side chains, in addition to replacement or deletion of one or more amino acids.

D. Genetic Vaccine Antigens

In certain embodiments, an immune response may be promoted by transfecting or inoculating an animal with a nucleic acid encoding an antigen comprising a CTL epitope modified in accordance with the invention. Such a nucleic acid can be designed using codons known to those of skill in the art, based on the chemical structure of the respective amino acids. One or more cells comprised within a target animal can then expresses the sequences encoded by the nucleic acid after administration of the nucleic acid to the animal. Thus, the vaccine may comprise a "genetic vaccine" useful for immunization protocols. A vaccine may also be in the form, for example, of a nucleic acid (e.g., a cDNA or an RNA) encoding all or part of the peptide or polypeptide sequence of an antigen. Expression in vivo by the nucleic acid may be, for example, by a plasmid type vector, a viral vector, or a viral/plasmid construct vector.

The nucleotide and protein, polypeptide and peptide encoding sequences for various antigens have been previously disclosed, and may be found at computerized databases known to those of ordinary skill in the art. One such database is the National Center for Biotechnology Information's Genbank and GenPept databases (found on the world wide web at ncbi.nlm.nih.gov). The coding regions for these known antigens may be amplified and/or expressed using the techniques disclosed herein or by any technique that would be know to those of ordinary skill in the art (e.g., Sambrook et al., 2001). Though a nucleic acid may be expressed in an in vitro expression system, in certain embodiments of the invention the nucleic acid comprises a vector for in vivo replication and/or expression.

E. Cellular Vaccine Antigens

In another embodiment, a cell expressing the antigen may be included in the vaccine. The cell may be isolated from a culture, tissue, organ or organism and administered to an animal as a cellular vaccine. Thus, the present invention contemplates a "cellular vaccine." The cell may be transfected with a nucleic acid encoding an antigen to enhance its expression of the antigen. Of course, the cell may also express one or more additional vaccine components, such as immunomodulators or adjuvants. A vaccine may comprise all or part of the cell.

In particular embodiments, it is contemplated that nucleic acids encoding antigens of the present invention may be transfected into plants, particularly edible plants, and all or part of the plant material used to prepare a vaccine, such as for example, an oral vaccine. Such methods are described in U.S. Pat. Nos. 5,484,719, 5,612,487, 5,914,123, 5,977,438 and 6,034,298, each incorporated herein by reference.

F. Vaccine Component Purification

A vaccine component, including an antigenic peptide in accordance with the invention, may be isolated and/or purified from chemical synthesis reagents, cell or cellular components. In a method of producing the vaccine component, purification may be accomplished by any appropriate technique that is described herein or well-known to those of skill in the art (e.g., Sambrook et al., 2001). Although preferred for use in certain embodiments, there is no general requirement that an antigenic composition of the present invention or other vaccine component always be provided in their most purified state. Indeed, it is contemplated that less substantially purified vaccine component, which is nonetheless enriched in the desired compound, relative to the natural state, will have utility in certain embodiments.

The present invention also provides purified, and in preferred embodiments, substantially purified vaccines or vaccine components. The term "purified vaccine component" as used herein, is intended to refer to at least one vaccine component (e.g., a modified peptide antigen), wherein the component is purified to any degree relative to its naturally-obtainable state, e.g., relative to its purity within a cellular extract or reagents of chemical synthesis. In certain aspects wherein the vaccine component is a wild-type or mutant protein, polypeptide, or peptide free from the environment in which it naturally occurs.

Where the term "substantially purified" is used, this will refer to a composition in which the specific compound forms the major component of the composition, such as constituting about 50% of the compounds in the composition or more. In certain embodiments, a substantially purified vaccine component will constitute more than about 60%, about 70%, about 80%, about 90%, about 95%, about 99% or even more of the compounds in the composition.

In further embodiments, a vaccine component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g., antigenicity), or assessing the number of polypeptides within a fraction by gel electrophoresis.

Various techniques suitable for use in chemical, biomolecule or biological purification, well known to those of skill in the art, may be applicable to preparation of a vaccine component of the present invention. These include, for example, precipitation with ammonium sulfate, PEG, antibodies and the like or by heat denaturation, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography ion exchange, gel filtration, reverse phase, hydroxylapatite, lectin affinity; isoelectric focusing and gel electrophoresis (see for example, Sambrook et al. 2001; and Freifelder, Physical Biochemistry, Second 1982, incorporated herein by reference).

Given that many DNA and proteins are known (see for example, the National Center for Biotechnology Information's Genbank and GenPept databases (found on the world wide web at ncbi.nlm.nih.gov)), or may be identified and amplified using the methods described herein, any purification method for recombinantly expressed nucleic acid or proteinaceous sequences known to those of skill in the art can now be employed. In certain aspects, a nucleic acid may be purified on polyacrylamide gels, and/or cesium chloride centrifugation gradients, or by any other means known to one of ordinary skill in the art (see for example, Sambrook et al. 2001 incorporated herein by reference). In further aspects, a purification of a proteinaceous sequence may be conducted by recombinantly expressing the sequence as a fusion protein. Such purification methods are routine in the art. This is exemplified by the generation of an specific protein-glutathione S-transferase fusion protein, expression in E. coli, and isolation to homogeneity using affinity chromatography on glutathione-agarose or the generation of a polyhistidine tag on the N- or C-terminus of the protein, and subsequent purification using Ni-affinity chromatography.

In particular aspects, cells or other components of a vaccine may be purified by flow cytometry. Flow cytometry involves the separation of cells or other particles in a liquid sample, and is well known in the art (see, for example, U.S. Pat. Nos. 3,826,364, 4,284,412, 4,989,977, 4,498,766, 5,478,722, 4,857,451, 4,774,189, 4,767,206, 4,714,682, 5,160,974 and 4,661,913). Any of these techniques described herein, and combinations of these and any other techniques known to skilled artisans, may be used to purify and/or assay the purity of the various chemicals, proteinaceous compounds, nucleic acids, cellular materials and/or cells that may comprise a vaccine of the present invention. As is generally known in the art, it is believed that the order of conducting the various purification steps may be changed, or that certain steps may be omitted, and still result in a suitable method for the preparation of a substantially purified antigen or other vaccine component.

G. Enhancement of Immune Response

The present invention includes a method of enhancing the immune response in a subject comprising the steps of contacting one or more lymphocytes with an antigen modified as is described herein. In certain embodiments, a modified antigen may be conjugated to or comprises an HLA anchor motif amino acids. In other embodiments, a composition comprising an antigen as described herein is contained in a mixture that comprises an additional immunostimulatory agent. Immunostimulatory agents include but are not limited to an additional antigen, an immunomodulator, an antigen presenting cell or an adjuvant. In other embodiments, one or more of the additional agent(s) is covalently bonded to an antigen or an agent, in any combination.

In certain embodiments, a lymphocyte contacted with a modified CTL epitope is comprised in an animal, such as a human. In certain embodiments, the animal is a human cancer patient, for example, a human breast cancer patient or a human prostate cancer patient. In a preferred aspect, the one or more lymphocytes comprise a T-lymphocyte. In a particularly preferred facet, the T-lymphocyte is a cytotoxic T-lymphocyte.

The enhanced immune response may be an active or a passive immune response. Alternatively, the response may be part of an adoptive immunotherapy approach in which lymphocyte(s) are obtained with from an animal (e.g., a patient), then pulsed with a composition comprising a modified antigenic composition. In this embodiment, the antigenic composition may comprise an additional immunostimulatory agent. The lymphocyte(s) may be obtained from the blood of the subject, or alternatively from tumor tissue to obtain tumor infiltrating lymphocyte(s) as disclosed in Rosenberg et al., 1986, incorporated herein by reference. In certain preferred embodiments, the lymphocyte(s) are peripheral blood lymphocyte(s). In a one embodiment, the lymphocyte(s) are administered to the same or a different animal (e.g., same or different donors). In another embodiment, the animal (e.g., a patient) has or is suspected of having a cancer, such as for example, a breast or prostate cancer. One type of such therapy is active immunotherapy.

In active immunotherapy, the antigen, for example, comprising a CTL epitope modified as described herein, is administered, generally with a distinct bacterial adjuvant (Ravindranath & Morton, 1991; Mitchell et al., 1990; Mitchell et al., 1993). For example, even with prior techniques, in melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anticarbohydrate antibodies.

H. Vaccine Administration

The manner of administration of a vaccine comprising an antigen prepared in accordance with the invention may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

A vaccination schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of antigens with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host.

Precise amounts of an active ingredient required to be administered depend on the judgment of the practitioner. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms of active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., inoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. In prophylactic embodiments, the vaccinations will normally be at from two to twelve week intervals, more usually from three to five week intervals. Periodic boosters at intervals of 1-5 years, usually three years, will be desirable to maintain protective levels of the antibodies.

The course of the immunization may be followed by assays for antibodies for the modified antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064 as illustrative of these types of assays.

I. Infectious Disease States

In addition to the treatment of cancer, the current invention is applicable to the treatment or prevention of diseases mediated by an infectious agent, for example, a bacteria, virus or parasite. In particular, by modulation of an immunologic response to a CTL epitope of an infectious agent, an immune reaction to the antigen bearing the given CTL epitope may be modulated for clinical benefit. Such CTL epitopes may be found and modified from viral and bacterial pathogens, as well as various parasitic organisms. Non-limiting examples of such causative agents which may be treated with the invention are presented below.

1. Viral Infections

Certain aspects of the current invention concern treatment or prevention of viral diseases by modulation of an immunologic response to viral infection. In particular, by identification and modification of a viral CTL epitope, as is described herein, certain therapeutic or prophylactic benefits may be obtained. Such viruses may enter or exit the body through the mucosal surfaces such as the following pathogenic viruses which are mentioned by way of example, influenza A, B and C, parainfluenza, paramyxoviruses, Newcastle disease virus, respiratory syncytial virus, measles, mumps, adenoviruses, adenoassociated viruses, parvoviruses, Epstein-Barr virus, rhinoviruses, coxsackieviruses, echoviruses, reoviruses, rhabdoviruses, lymphocytic choriomeningitis, coronavirus, polioviruses, herpes simplex, human immunodeficiency viruses, cytomegaloviruses, papillomaviruses, virus B, varicella-zoster, poxviruses, rubella, rabies, picornaviruses, rotavirus and Kaposi associated herpes virus.

2. Bacterial Infections

The invention may also find use in the treatment or prevention of a disease mediated by bacterial infection. As indicated, this may be carried out by identifying and modifying a bacterial CTL epitope and administering this to an individual in need thereof. Again, this may be done either in response to an ongoing bacterial disease and/or for the prevention of such a disease. Examples of such bacterial infections that could be treated or prevented with the invention, include, but are not limited to, the 83 or more distinct serotypes of pneumococci, streptococci such as *S. pyogenes, S. agalactiae, S. equi, S. canis, S. bovis, S. equinus, S. anginosus, S. sanguis, S. salivarius, S. mitis, S. mutans*, other viridans streptococci, peptostreptococci, other related species of streptococci, enterococci such as *Enterococcus faecalis, Enterococcus faecium*, Staphylococci, such as *Staphylococcus epidermidis, Staphylococcus aureus*, particularly in the nasopharynx, *Hemophilus influenzae, pseudomonas* species such as *Pseudomonas aeruginosa, Pseudomonas pseudomallei, Pseudomonas mallei, brucellas* such as *Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocordia asteroides, Bacteroides* species, *Actinomycetes* species, *Treponema pallidum, Leptospirosa* species and related organisms. The invention may also be useful against gram negative bacteria such as *Klebsiella pneumoniae, Escherichia coli, Proteus, Serratia* species, *Acinetobacter, Yersinia*

*pestis, Francisella tularensis, Enterobacter* species, *Bacteriodes* and *Legionella* species and the like.

3. Parasitic Infections

In addition, the invention may prove useful in controlling protozoan or macroscopic infections by organisms such as *Cryptosporidium, Isospora belli, Toxoplasma gondii, Trichomonas vaginalis, Cyclospora* species, for example, and for *Chlamydia trachomatis* and other *Chlamydia* infections such as *Chlamydia psittaci*, or *Chlamydia pneumoniae*, for example. Of course it is understood that the invention may be used on any pathogen for which a CTL epitope can be identified and modified in accordance with the invention.

J. Vectors

In certain embodiments of the invention, a modified CTL epitope-containing antigen may be administered to a patient in need thereof in the form of a transformation vector. For example, such vectors may be administered to a patient to achieve expression of the epitope or may be administered as cells which have been transformed with the vector. The transfection of cells may thus be used, in certain embodiments, to recombinantly produce one or more vaccine components for subsequent purification and preparation into a pharmaceutical vaccine. In other embodiments, the nucleic acid is transfected into a cell and the cell administered to an animal as a cellular vaccine component.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The nucleic acid encoding the antigenic composition or other vaccine component may be stably integrated into the genome of the cell, or may be stably maintained in the cell as a separate, episomal segment of DNA. Such nucleic acid segments or "episomes" encode sequences sufficient to permit maintenance and replication independent of or in synchronization with the host cell cycle. Vectors and expression vectors may contain nucleic acid sequences that serve other functions as well and are described infra. How the expression construct is delivered to a cell and where in the cell the nucleic acid remains is dependent on the type of expression construct employed.

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. Promoter for use in different cell types, including mammalian and human cells, are well known to those of skill in the art.

Numerous different types of vectors for transformation of cells are known. The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). For example, a modified CTL epitope could be encoded by a nucleic acid or other components such as, for example, an immunomodulator or adjuvant, could be encoded by the vector. Many types of viral vectors are known and could be used with the invention, including adenoviral vectors, adeno-associated viruses (AAV), retroviral vectors or other types of viral vectors.

Suitable methods for nucleic acid delivery for transformation of cells are also well known to those of skill in the art. Examples of such methods known to those of skill in the art include, but are by no means limited to: calcium phosphate precipitation, use of DEAE-dextran followed by polyethylene glycol, direct sonic loading and liposome-mediated transfection. Any such of these methods or other methods may thus be used with the invention.

IV. SCREENING FOR MODULATION OF IMMUNOGENICITY

In certain aspects of the invention, assays for modulation of immunogenicity may be used for the assessment of particular modified antigen epitopes. In this manner, modifications may be optimized for the desired immunologic effect. For example, assays of CTL activity may be used following administration of modified antigens. CTL activity can be assessed by methods described herein or as would be known to one of skill in the art. Such assays may find use in accordance with the invention for the assessment of modified CTL epitopes for the ability to modulate immunogenicity. For example, CTLs may be assessed in freshly isolated peripheral blood mononuclear cells (PBMC), in a phytohaemaglutinin-stimulated IL-2 expanded cell line established from PBMC (Bernard et al., 1998) or by T cells isolated from a previously immunized subject and restimulated for 6 days with antigen using standard 4 h $^{51}Cr$ release microtoxicity assays. One type of assay uses cloned T-cells.

Cloned T-cells have been tested for their ability to mediate both perforin and Fas ligand-dependent killing in redirected cytotoxicity assays (Simpson et al., 1998). The cloned cytotoxic T lymphocytes displayed both Fas- and perforin-dependent killing. Recently, an in vitro dehydrogenase release assay has been developed that takes advantage of a new fluorescent amplification system (Page et al., 1998). This approach is sensitive, rapid, reproducible and may be used advantageously for mixed lymphocyte reaction (MLR). It may easily be further automated for large scale cytotoxicity testing using cell membrane integrity, and is thus could be used in the present invention. In another fluorometric assay developed for detecting cell-mediated cytotoxicity, the fluorophore used is the non-toxic molecule alamarBlue (Nociari et al., 1998). The alamarBlue is fluorescently quenched (i.e., low quantum yield) until mitochondrial reduction occurs, which then results in a dramatic increase in the alamarBlue fluorescence intensity (i.e., increase in the quantum yield). This assay is reported to be extremely sensitive, specific and requires a significantly lower number of effector cells than the standard $^{51}Cr$ release assay.

In certain aspects, T helper cell responses can be measured by in vitro or in vivo assay with peptides, polypeptides or proteins. In vitro assays include measurement of a specific cytokine release by enzyme, radioisotope, chromaphore or fluorescent assays. In vivo assays include delayed type hypersensitivity responses called skin tests, as would be known to one of ordinary skill in the art.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Modified Epitopes

A modified epitope was created based on the CTL epitope from the HER-2 protooncogene protein product. The sequence of the native peptide (SEQ ID NO:2) is as follows:

| 1 | 2 | 3 | 4 | 5 | 6 | 7 | 8 | 9 |
|---|---|---|---|---|---|---|---|---|
| K | I | F | G | S | L | A | F | L |

A preliminary analysis of the possible orientation of the amino acids in this peptide when bound to HLA-A2 indicated that Gly4 and Ala1 were good candidates for $CH_2$-extension because Gly4 lacks a side chain, and Ala7 has one $CH_3$ group as a side chain. Since Ala7 is preceded by Leu6 and followed by Phe8 and Leu9, it was hypothesized that the $CH_3$ side chain in Ala7 points either sideways or upwards (Leu9, down, Phe8 side or up and Ala7, side or up). Based on this, it was decided to replace the Ala7 with the unnatural aminoacids: γ-aminobutyric (Abu) which has 1 $CH_2$ group extension compared with Ala7 (designated herein A7.1), norvaline (NVal) which has 2 $CH_2$ groups extending linearly from Ala7 (designated herein A7.2) and norleucine (Nleu) which has 3 $CH_2$ groups extending from Ala to the side chain of Ala7 (designated herein A7.3). The same approach was used for extending the Gly4 with 4 $CH_2$ groups (+1, +2, +3, +4) by replacing successively Gly4 with Ala, ABu, NVal and Nleu.

A second approach to this $CH_2$ modification is to shorten the side chain in Phe8 ("attenuation") by replacement of Phe8 with IsoPhe8. IsoPhe lacks the $CH_2$ group between the phenol ring and the peptide bond.

Molecular modeling showed that indeed $CH_2$ extension at Ala7 lead to a C-chain which is oriented upward (i.e., toward the TCR). The structures of E75 (Ala), A7.1 (Abu), A7.2 (Nval), A7.3 (Nleu) in the HLA-A2 were modeled by downloading the coordinates of the HLA-A2 native structure (Saper, 1999) from the Brookhaven protein database. This file was used as a template for manipulations with the Swiss Model program (Peitsch, 1997), available through the Expasy web site. A bound Tax peptide was mutated manually to yield the bound E75 peptide. The new structure was optimized and energy minimized with the GROMOS96 implementation or the Swiss-Pdb Viewer. The van der Waals radii or the equivalent atoms were depicted as spheres. The CH2-extended Ala-side chains were presented in yellow (structure not shown). The HLA-A2-peptide structure was presented for each peptide in a corresponding box.

The possibility of inducing side chain changes is controllable. For example Lys1 can be replaced with ornithine (−1 $CH_2$). Arg can be replaced by citrulline, etc. Thus in E75 successive attenuation could be obtained by removal of 5 $CH_2$ groups in Lys1, Phe3, Leu6, Ala7, and Phe8. Gradual attenuation can be achieved by successful removal of these groups. This approach can be used for other tumor peptides which bind not only HLA-A2, but also other MHC-(class I and class II) molecules.

Example 2

Modeling of the E75-HLA-A2 Complex

E75-HLA-A2, models were generated by replacement of the HTLV-1 (Tax) peptide with E75 (Garboczi et al., 1996; Madden et al., 1993; Baker et al., 2000; Gillogly et al., 2000). Tax shows the highest structural similarity of the models available in public databases. The Tax peptide: L L F G Y P VYV (SEQ ID NO:1) is similar to E75: KIEG SL AFL, (SEQ ID NO:2) with respect aliphatic side chain extension in the first 4 and the last 3 amino acids, with only Lys1 and Phe8 differing by $NH_3$ and OH group extensions. The central area of Tax is currently under intense scrutiny, with the analog P6A showing even more similarity in the core with E75 (Leu6) (Baker et al., 2000).

Here, the inventors replaced Ala7 with the unnatural amino acids γABU, NVal, and NLeu, because the side chains of these amino acids linearly extend the $CH_3$ group of Ala7, with 1, 2, and 3 $CH_2$ groups, respectively. This was deemed preferred over the replacements with Val and ILe, because their branched chains are less flexible. The HLA-A2-E75 structure was modeled using pdb entry 1BD2, an HLA-A2 crystal structure with bound Tax peptide and was analyzed for accessible surface area using the program GETAREA 1.1. The results indicate no significant overall changes in accessible surface area comparing the initial structure Tax HLA-A2 from structures of pdb versus the model structures and no significant change between model structures. This is compatible with the hypothesis that large conformational changes do not occur upon binding of any of Ala7 variant peptides. Thus it was indicated that it was likely that this would allow for TCR specific for E75 to bind the peptide. The surface areas calculated for each structure were: (in Å): Starting structure: (Tax) 18723.12 Å; (HER-2): Ala: (E75) =18707.55 Å, γAbu: (A7.1), 18737.80 Å, NVal: (A7.2), 18748.92 Å, NLeu: (A7.3), 18775.04 Å. Therefore there is a very small change in the surface (0.036%) between E75 and A7.3.

Example 3

Confirmation of CTL Epitope Modification Effect

The $CH_2$ side chains of the Ala7(E75=A7.0) and γABU7 (A7.1) point sideways while the side chains of NVal (A7.2) and of NLeu point upwards. Since Gly4 lacks side chains, it is likely that addition of $CH_2$ side chains in Gly4 by replacement with Ala, γAbu, NVal, and Nleu will lead to peptide with $CH_2$ side chains pointing upwards and/or sideways, creating new contacts for TCR. The fact that the substitution Gly to NVal is immunogenic was demonstrated by the ability of peptide G4.3 to induce both IFN-γ and IL-2 at stimulation of PBMC. A7.1, A7.2, A7.3 were of similar although slightly lower HLA-A2 stabilizing ability, as determined by on- and off-kinetics.

Example 4

Priming with $CH_2$ Extended E75 Analogs Induced High Levels or IFN-γ and IL-2 in Weak E75-Responder PBMC To establish the ability of $CH_2$-E75 to activate T cells, the ability of A7.2, A7.3 and G4.3 to activate induction of IFN-γ at priming was determined. Two donors were selected based on their weak ability to respond to E75 priming even in the presence of IL-12. FIGS. 1A and 1B shows that each of the A7.2, A7.3, G4.3 at 25 μM on autologous DC induced higher levels of IFN-γ than E75 in both donors tested. These results were confirmed with Donor 4, known to respond to E75 by rapid IFN-γ induction. FIG. 1C shows that peptide F8-1 induced lower levels of IFN-γ than E75. IsoPhe lacks the intermediate $CH_2$ group of Phe between the benzene ring and the peptide chain, thus is 1 $CH_2$ "shorter" than Phe8.

Figure 2:
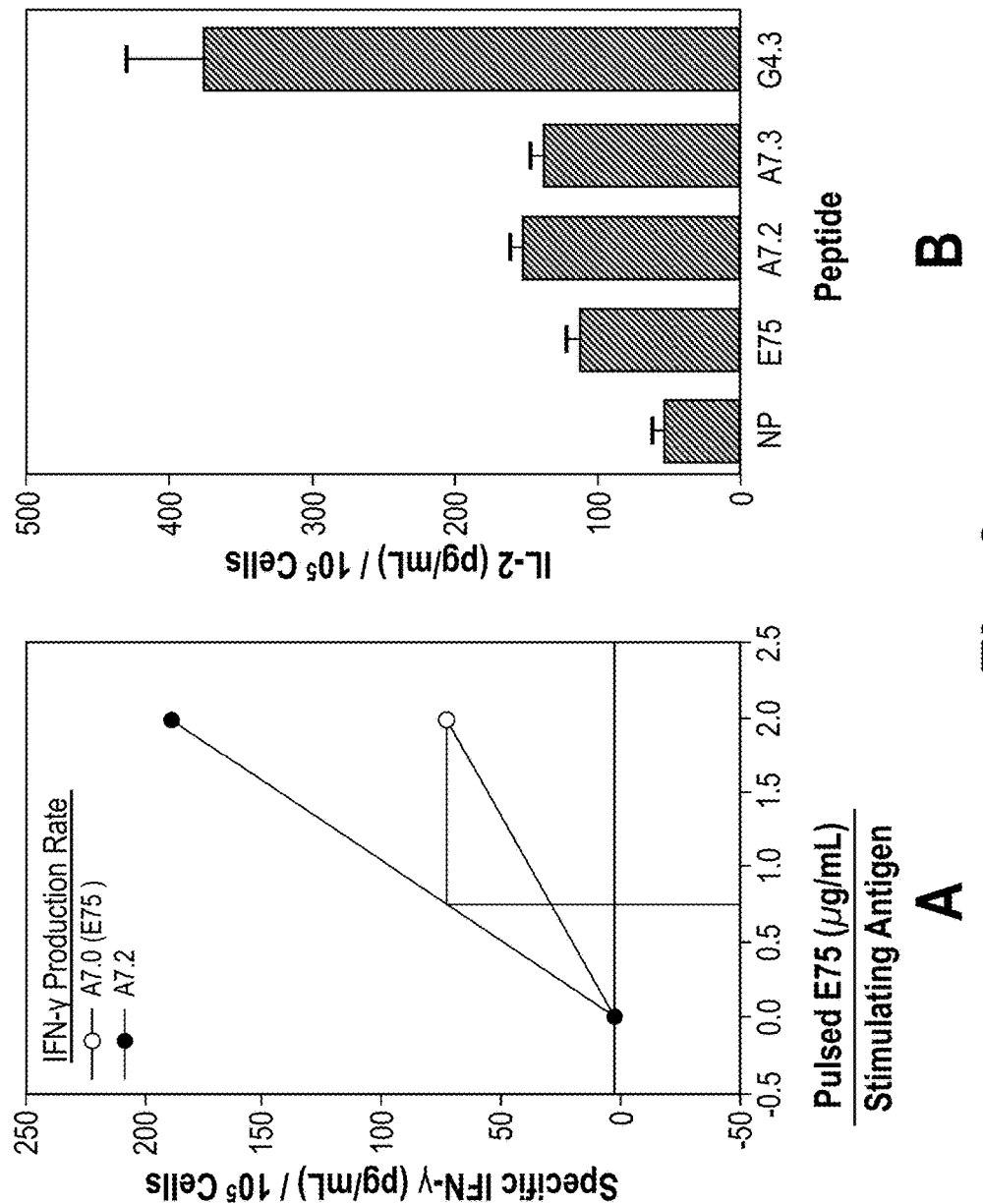

To address whether $CH_2$-E75-activated T cells recognized E75, E75-primed and A7.2-primed T cells were cultured in low concentrations of IL-2 (40-60 IU/ml) for one week, rested, and tested for their ability to respond to E75 within 16 h at a lower exogenous pulsed concentration 2 μg/ml. FIG. 2A shows that at 2 μM, A7.2-primed T cells responded to E75 with 3-fold higher levels of IFN-γ than E75-primed T cells. This suggested that A7.2-primed T cells recognized E75 with higher affinity than E75-primed T cells. To address whether $CH_2$-E75 induce higher levels of IL-2 than E75, all analogs were tested again in Donor 1 in the same study. FIG. 2B show that G4.3 induced high levels of IL-2 in this donor, compared with E75, A7.2, and A7.3.

Example 5

Priming with $CH_2$ Extended Analogs Induced-E75-Specific CTL of Higher Avidity for E75 than Priming with E75

Figure 3:
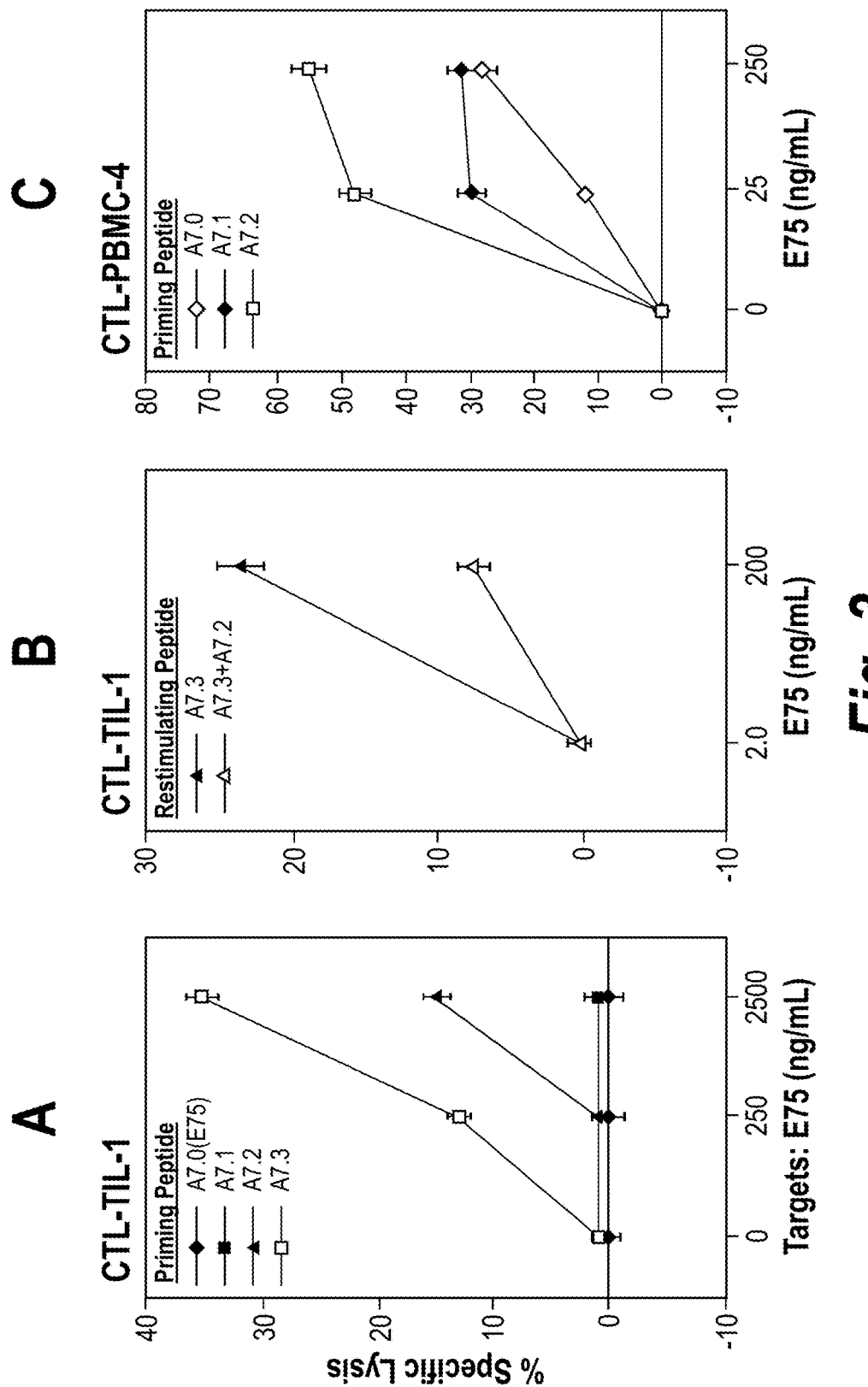

To address whether A 7.1, A 7.2 and A7.3 induced lytic effectors, their ability to activate lytic function in CD8+ cells isolated from TIL of an HLA-A2$^+$ ovarian patient was tested. T2 were used to present peptides to minimize the cross-reactivity of TIL with allo-DC. FIG. 3A show that the affinity for E75 of CTL primed with $CH_2$-E75 decreased in the order A7.3>A7.2>A7.1=A7.0. A7.0 and A7.1 stimulated CTL-TIL did not recognize E75. Restimulation of A7.3-induced CTL with A7.3 enhanced their affinity for E75 to the 200 nM level (FIG. 3B) while an additional stimulation with A7.2 increased their sensitivity for E75 at 50 nM level. This sensitivity is at least 100-fold higher than the optimal sensitivity of E75-induced CTL (5000-25000 nM) (zum Buschenfelde et al., 2000; Anderson et al., 2000). To address whether A7.2 and A7.3 activate lytic function of peripheral T cells, the ability of A7.3, A7.2 and A7.0 (E75) to activate E75-specific cytolysis was tested. Similar results were obtained with Donor 4 (FIG. 3C). FIG. 3C shows that A 7.3-induced CTL-recognized E75 at 25 nM exogenous pulsed concentration with higher affinity that E75-primed CTL.

Example 6

Attenuation of Signaling by $CH_2$ Deletion

Figure 4:
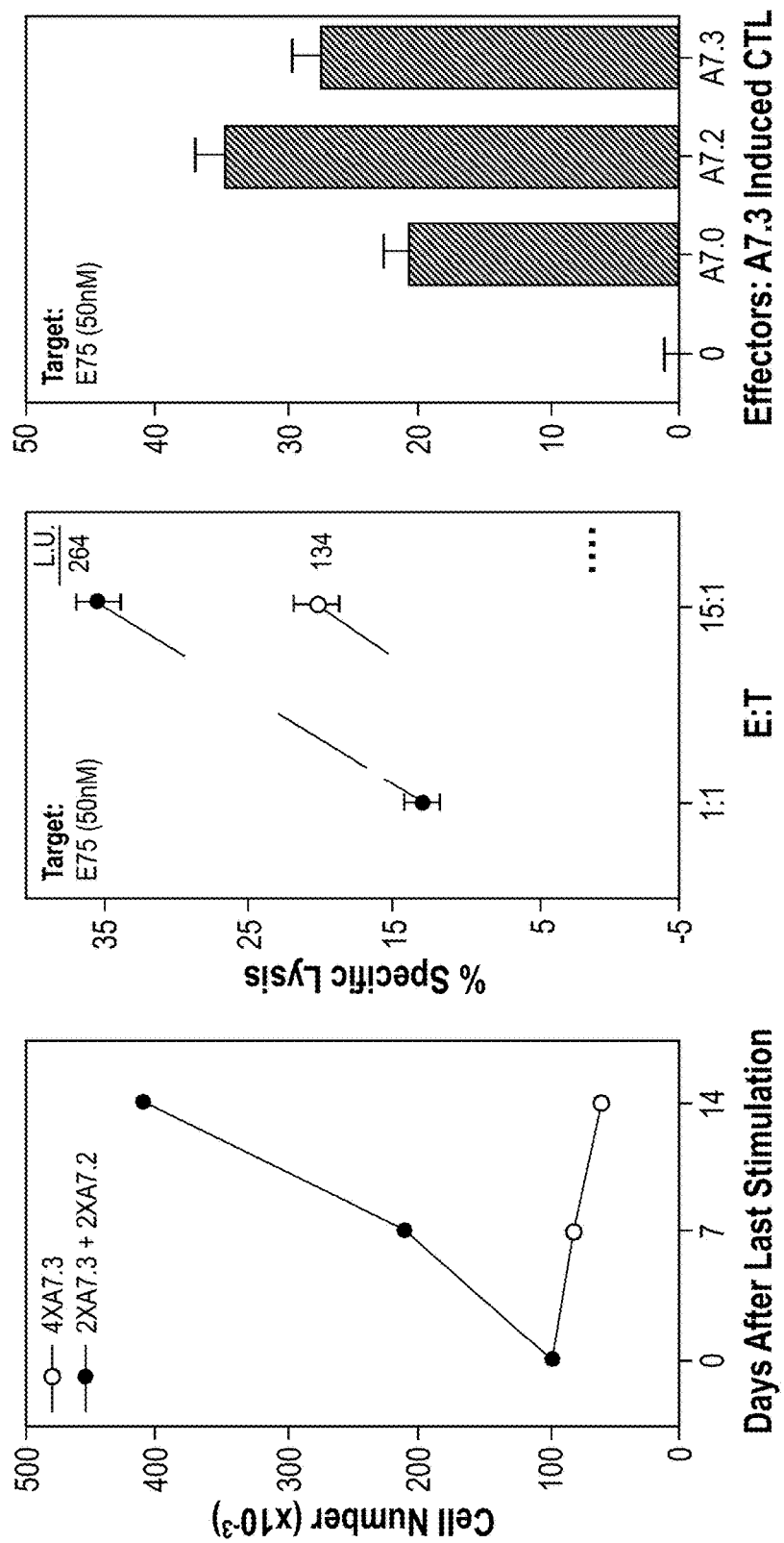

As A 7.3 activated CTL decreased in numbers at subsequent restimulations with A7.3, it was investigated whether attenuation of signaling by $CH_2$ deletion can increase their numbers. Two times stimulated (2×A7.3) cells were restimulated two more times, in parallel, with A7.2 or A7.3. A7.2 stimulated cells increased in numbers compared with A7.3-stimulated cells. 2×A7.3 to 2×A7.2 stimulated cells contained a higher number of E75-specific lytic effectors compared with 4×A7.3 cells, as indicated by lytic units, LU (FIG. 4B). These results demonstrated that attenuation of TCR signaling using less $CH_2$-extended E75 enhanced the overall yields of high affinity CTL. Since the numbers of CD8$^+$ cells induced by the schedule 2×A7.3 to 2×A7.2 were 4 times higher than the numbers of CD8$^+$ cells induced by the schedule 4×A7.3 and the number of E75-specific LU induced by the first schedule was two times higher, this suggests an 8-fold (4×2) increase in the number of E75-lytic specific effectors by alternation of stronger and weaker signaling.

Example 7

Rested (Post-Effector) A7.3-Induced CTL Required Restimulation for Activation of Lytic Function To elucidate whether A7.3-induced CTL express lytic function without stimulation, A 7.3 induced CTL were rested (posteffectors) and restimulated with A7.3, A7.2 and A7.0, pulsed on autologous DC, or with autologous DC which were not pulsed with peptide group (0) in the absence of IL-2. A7.3-CTL were tested 30 h later for recognition of E75 pulsed on $^{51}$Cr-labelled T2 cells. A7.3-CTL required antigen-stimulation for expression of lytic function because they responded to either E75 or to A7.2 and A7.3 analogs by expression of lytic function. Although somewhat higher levels of lytic activity were induced in A7.3 CTL by restimulation with A7.2, confirming the results in FIG. 4B, the fact that A7.3-induced CTL activated a lytic function in response to E75 suggested that such CTL may be activated in response to tumor antigen.

Example 8

A7.3-Induced CTL Recognized Endogenously Presented E75

Figure 5:
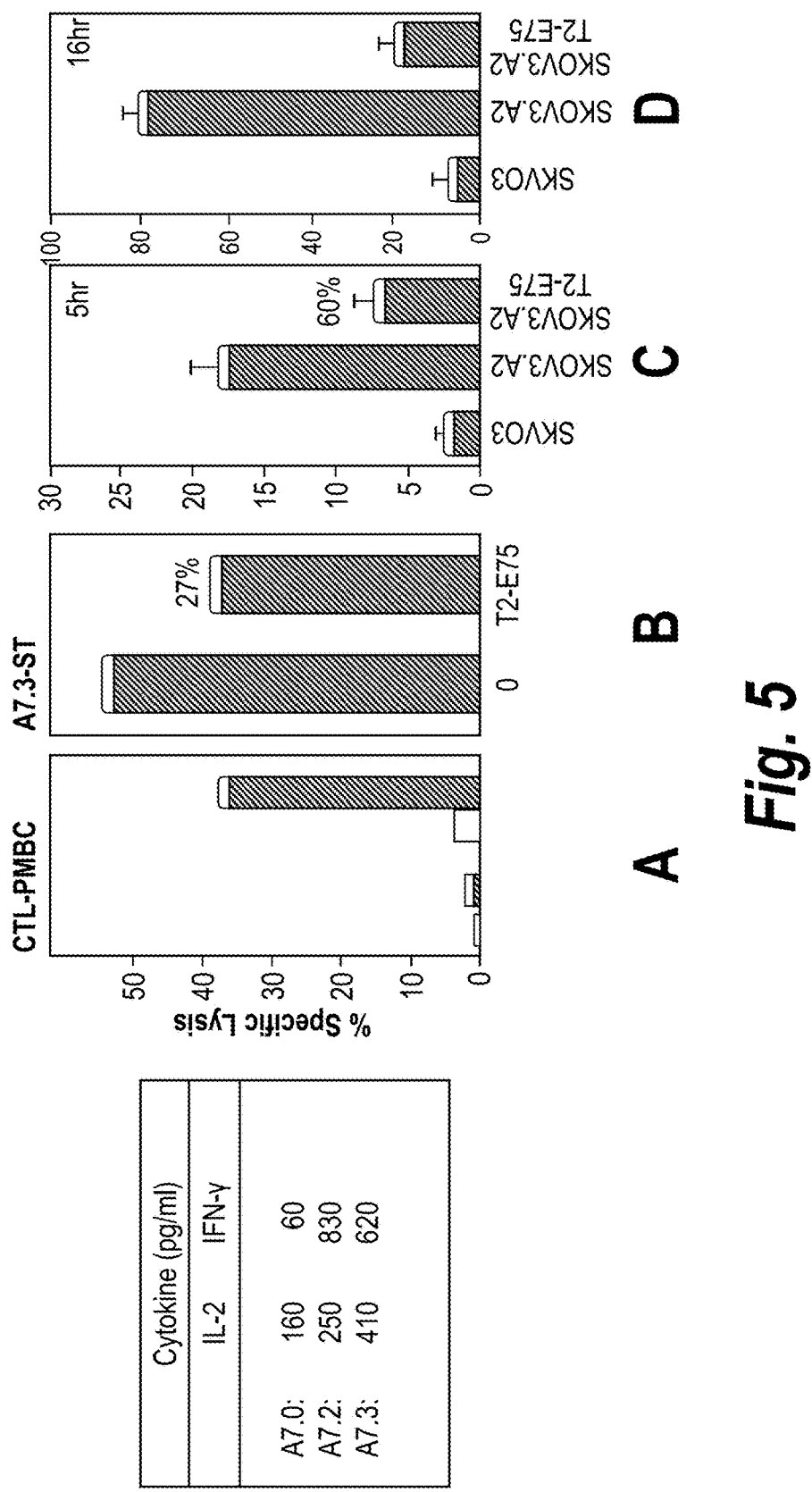

E75-induced CTL, in some instances, failed to recognize tumor cells presenting E75 because of their low affinity for the antigen. To verify that A7.3-induced CTL recognize E75 with high avidity, Donor 3 CTL-3$^{hi}$ were induced after priming with E75 and re stimulation with A7.3 from a Donor 3 which responded weakly to E75 (CTL-3$^{lo}$), (Zaks and Rosenberg, 1998). In this donor A7.2 was a stronger inducer of IFN-γ while A7.3 a stronger inducer of IL-2 than A7.2 (FIG. 5). CTL-3 recognized E75 with high avidity. To verify that CTL-3$^{hi}$ recognized endogenous E75 with high avidity T2 were pulsed with 100 nM E75 and used to inhibit lysis. To address whether A7.3-induced CTL recognize ovarian tumor SKOV3.A2, the inventors performed cold-target inhibition experiments (FIG. 5B, 6C, 6D). CTL-TIL-lysed SKOV3.A2 (HLA-A2$^!$), but not SKOV3 cells in the presence of unlabelled T2 cells which were not pulsed with peptide. When T2 cells were pulsed with E75, SKOV3.A2 lysis was inhibited by 60% in a 5 h CTL assay. T2-E75 continued to inhibit SKOV3.A2 lysis at the same or even higher levels when the assay was continued for 16 h, suggesting that diversion of E75-specificity was a stable effect.

Example 9

Stimulation of T-Cells with "Attenuated E75" (F8-1) Increased Expansion of CD62L+ Cells Compared with E75

Figure 6:
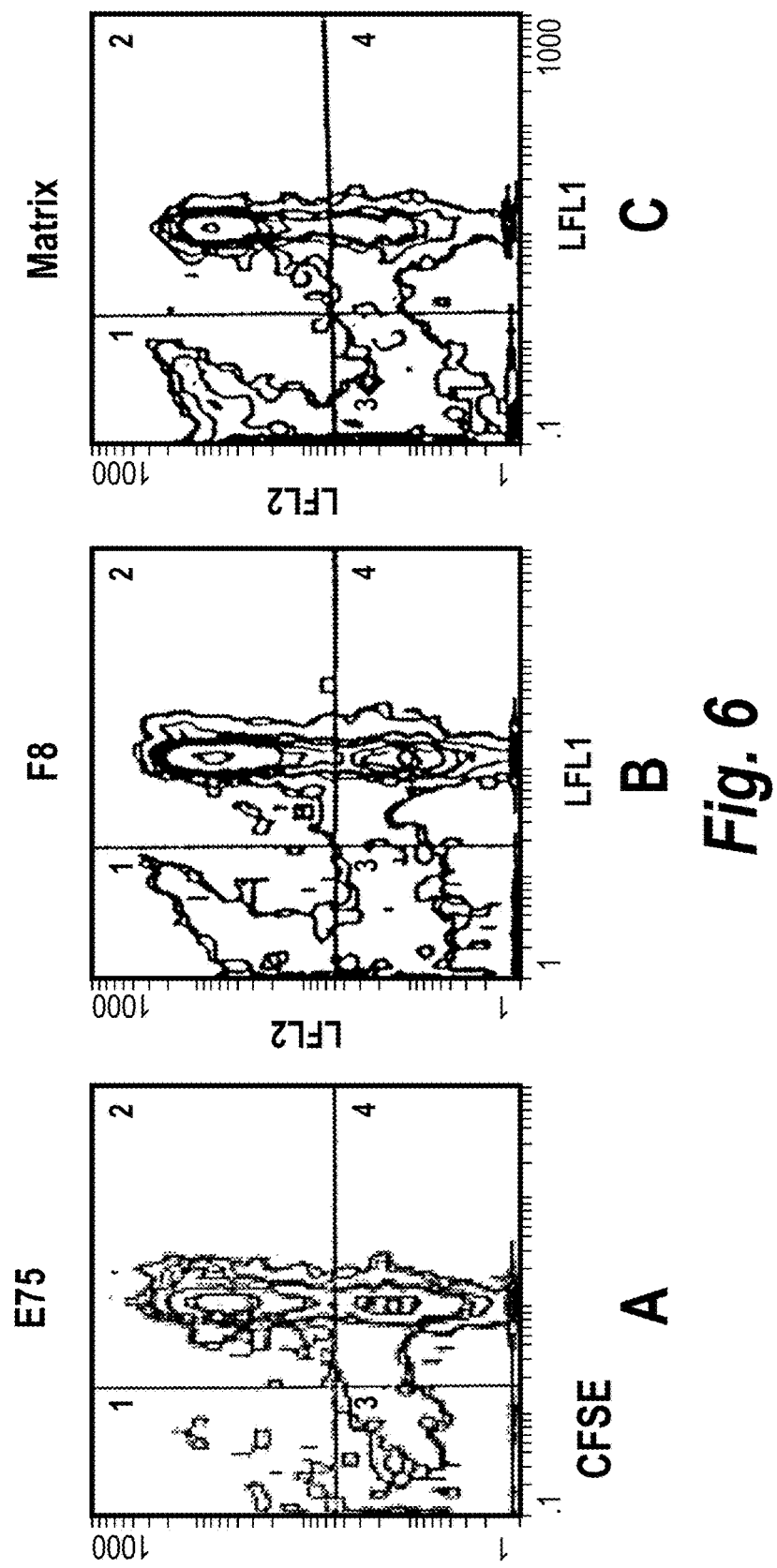

To address whether "attenuated E75" analogs activate T-cells, the inventors used F8-1. As control "attenuated E75," the entire $CH_2$-0H group in the position 5 was deleted by replacing Ser with Gly (analog S5.0). Isolated CD8+ cells from Donor 1 were labeled with CFSE, then stimulated with E75, S5.0, F8.1 and as positive control with the influenza matrix CTL epitope M1: 58-66, pulsed on autologous DC. IL-2 was added at 100 IU/ml (16 Cetus U) two days later. Cells were maintained in culture for 20 additional days, then stained with PE-conjugated mAb to CD62L and examined by two color fluorescence analysis. FIG. 6 shows that F8-1 induced a significant increase in the CD62L+ cells, representing 10.8% of the resulting population, while in E75 and S.5.0-stimulated cells, they represented only 3.5% and 4.8%, respectively. CD62L is down regulated during the first 2-3 divisions, then re-expressed at higher levels after 6 divisions (Baker et al., 2000). Lack of CFSE fluorescence in live CD62L+ cells suggested that these cells underwent at least 6-7 divisions (Baker et al., 2000). In positive control, MI stimulated cells CD62L+ CFSE cells were 21%. This suggested that under identical conditions F8-1 enhanced proliferation of a CD62L+ sub-population compared with E75.

Example 10

Stimulation of E75-Specific CTL Line (F42SK) with "Attenuated E75" F8-1 Induced Significantly Higher Levels of BcL-2 and Bcl-XL than Wild-Type E75, and $CH_2$-Extended A7.3

To address whether "attenuated E75" enhanced survival proteins expression, the E75-specific CTL line F42SK (Gillogly et al., 2000) was used as a target developed by stimulation of T cells from a healthy donor which responded weakly to E75, with an "enhancer agonist" designated F42, developed by replacement of Ser5 with Lys5. Replacement of a OH group with a charged residue enhanced the affinity of the analog for TCR illustrated by higher IFN-γ induction by F42 than E75. F42SK-CTL recognized exogenous pulsed E75 although with lower affinity (5000 ng/ml); they also recognized SKOV3.A2 cells in the context of HLA-A2, as demonstrated by cold-target inhibition and antibody-inhibition assays (Gillogly et al., 2000).

Figure 7:
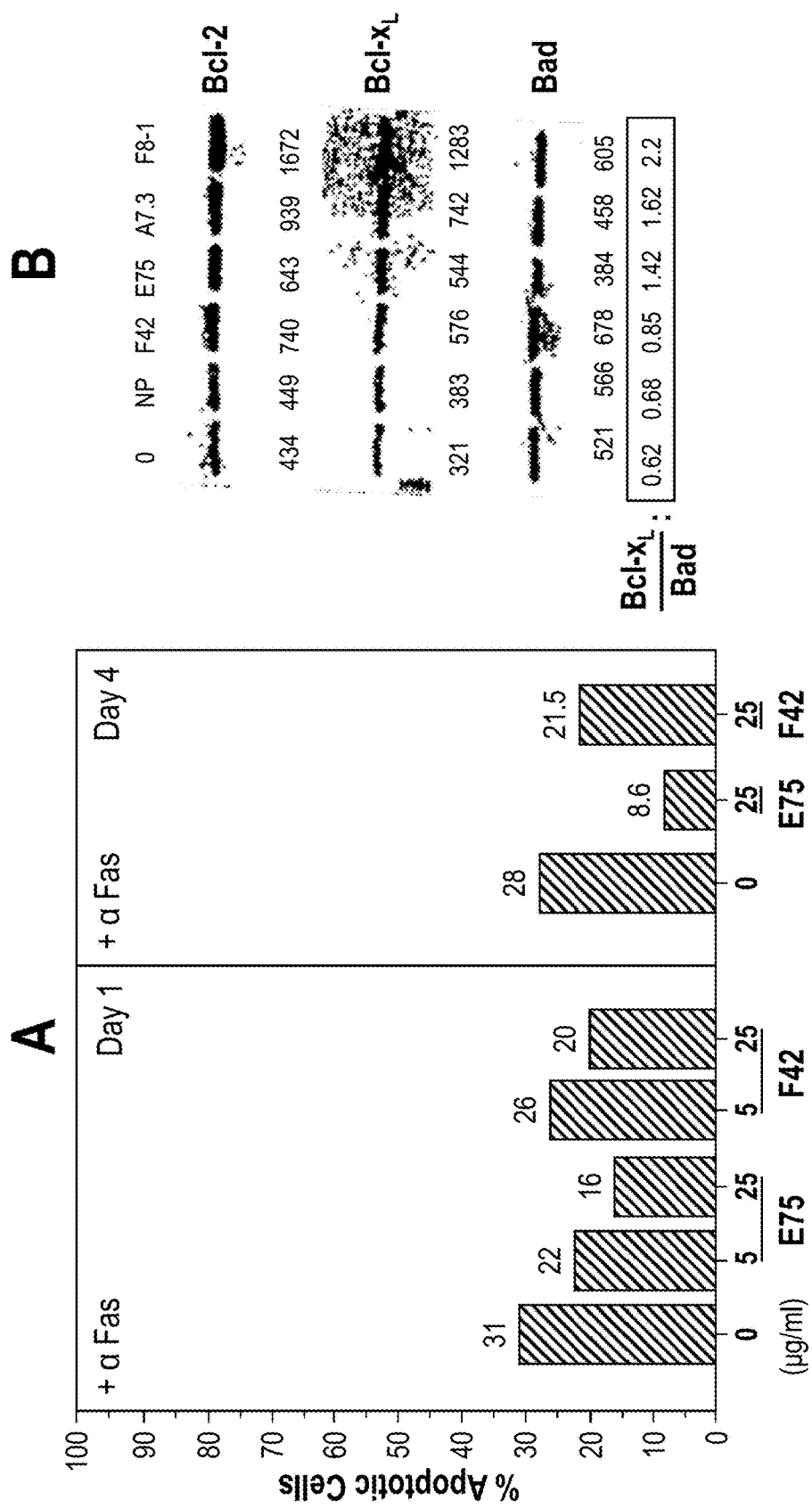

F42SK-CTL were subjected to multiple rounds of F42 stimulation. The responders never encountered A7.3 or F8-1. F42SK-CTL showed residual Fas-mediated apoptosis (≥30%). E75 induced more protection than the inducer F42 from residual apoptosis induced by a Fas mAb (FIG. 7A). Since apoptosis resistance in day 4 stimulated T cells is mainly due to the intrinsic pathway (Roy and Nicholson, 2000; Krammer, 2000) and resistance to Fas induced apoptosis was suggestive of TCR induced protection, the inventors investigated the effects of E75, and F42 in upregulation of Bcl-2 and Bcl-XL and Bad. The effects of A7.3 and F8-1 tested in parallel. FIG. 7B show that F42 and E75 had similar effects in upregulating Bcl-XL and Bcl-2. F42 was a slightly stronger up-regulator of Bcl-2 than E75. Their effects on Bcl-XL were similar. E75 was a stronger inhibitor of Bad than F42. Both A7.3 and F8-1 were significantly stronger stimulators for up-regulation of Bcl-2 and Bcl-XL than F42. F8-1 was the strongest inducer of Bcl-2 and Bcl-XL. Since A7.3 differs from E75 by addition of 3 $CH_2$ groups, F8-1 differs from E75 by deletion of 1 $CH_2$ group, these results demonstrate that E75-specific CTL are highly sensitive to modulation of $CH_2$ length by upregulation of pro survival molecules.

Example 11

Materials and Methods

Cells, Abs, and Cytokines

HLA-A2+ and PBMC were obtained from completely HLA-typed healthy volunteers. T2 cells, ovarian SKOV3, SKOV3.A2 cells, and indicator tumors from ovarian ascites were as described (Lee et al., 2000; Anderson et al., 2000; Fisk et al., 1995). mAb to CD3, CD4, CD8 (Ortho Diagnostics, Rantory, N.J.), CD13 and CD14 (Caltag Laboratories, San Francisco, Calif.), and HLA-A2 (clone BB7.2; American Type Culture Collection, Manassas, Va.) were either unconjugated or conjugated with FITC or PE. antigen expression by dendritic cells (DCs) and T cells was determined by FACS analysis using a flow cytometer (EPICS-Profile Analyzer; Coulter Electronics, Hialeah, Fla.). GM-CSF of specific activity ($1.25 \times 10^7$ CFU/250 mg) was from Immunex, Seattle, Wash.; TNF-α of specific activity ($2.5 \times 10^7$ U/mg) was from Cetus (Emeryville, Calif.); IL-4 of specific activity ($5 \times 10^6$ IU/mg) was from Biosource International (Camarillo, Calif.); IL-2 of specific activity ($18 \times 10^6$ IU/mg) was from Cetus; IL-12 of specific activity ($5 \times 10^6$ U/mg) was a kind gift from Dr. S. Wolf (Department of Immunology, Genetics Institute, Cambridge, Mass.). The anti-human-Fas mAb CH11 was purchased from Upstate Biotechnology (Lake Placid, N.Y.). mAb to actin, Bcl-2, Bcl-$x_L$, and Bad were purchased from Santa Cruz Biotechnology (Santa Cruz, Calif.). All other specific mAb and isotype controls were obtained from BD PharMingen (San Diego, Calif.).

Synthetic Peptides

Peptides E75 (HER-2: 369-377) and its mutated analogs were used and are given in Table II. To facilitate presentation, E75 variants mutated at Ser5 are abbreviated based on the position and the substitution. For example, the variant in which serine (S) was replaced by alanine (A) is S5A and the variant in which serine was replaced with glycine (G) is S5G. A7.3, in which the alanine side chain was extended with two methylene groups, was obtained by replacement of Ala with Norleucine (linear side chain). F8-1 was obtained by replacing of Phe8 with isophenylalanine (IsoPhe) (1 $CH_2$) deletion. All peptides were prepared by the Synthetic Antigen Laboratory of M. D. Anderson Cancer Center (Houston, Tex.) and purified by HPLC. The purity of the peptides ranged from 95-97%. Peptides were dissolved in PBS and stored frozen at −20° C. in aliquots of 2 mg/ml.

Molecular Modeling of the Peptide: HLA-A2 Complex

The coordinates of the native HLA-A2 structure (Garboczi et al., 1996; Saper et al., 1999; Berman et al., 2000) were downloaded from the Brookhaven protein database (ID number: 3HLA). This file was used as a template for manipulations with the Swiss Model (Peitsch et al., 1997) program available through the Expasy web site. The Tax peptide bound to the HLA-A2 (Hausman et al., 1999) was mutated manually to yield the bound E75 peptide and the Ala5, Gly5, and Lys5 variants. Each new structure was submitted for energy minimization with the GROMOS96 implementation of the Swiss-PdbViewer. Solvent-accessible surface area was calculated with the GETAREA1.1 online program with the default probe radius, set at 1.4 Å.

T Cell Stimulation by Peptide Pulsed DC

DCs generated from peripheral blood were plated at $1.2 \times 10^5$ cell/well in 24-well culture plates and pulsed with peptides at 50 μg/ml in serum-free medium for 2 h before the addition of responders, as described (Lee et al., 2000; Anderson et al., 2000). E75-induced and S5K-induced CTL lines were maintained by periodic stimulation with peptide pulsed on DCs, followed by expansion in the presence of irradiated feeder cells and PHA. The number of cells expressing a TCR that was specific for HLA-A2 bound to the E75 peptide (E75-TCR+ cells) was performed using E75 dimers (dE75) prepared as described in the manufacturer's instructions. Empty HLA-A2:IgG dimers were obtained from BD Pharmingen. Control without peptide dimers not pulsed with peptide (NP) were prepared in parallel and tested in the same study. Positive control influenza matrix peptide M1 (58-66) dimers (dM1) were prepared simultaneously and used in the same study. For analysis, cells were incubated in parallel with dNP, and dE75 followed by PE-conjugated anti-mouse IgG1. Intracellular expression of Bcl-2 was determined, following manufacturer's instructions using FITC-conjugated Bcl-2, Ab, and a matched FITC-conjugated isotype control.

CTL and Cytokine Assays

Recognition by CTL of peptides used as immunogens was performed as described (Fisk et al., 1995). Recognition of E75 and of its variants was considered specific when the percent specific lysis of T2 cells pulsed with E75 minus the SD was higher by at least 5% than the percentage of specific lysis of T2 cells that had been pulsed with peptide plus the SD, as described (Knutson et al., 2001). A significant increase/decrease in CTL activity was defined as an increase/decrease of >20% in the lysis of T2 cells pulsed with peptide by variant induced CTL compared with wild-type E75-induced CTL. Similarly, a significant increase in IFN-γ induction was defined as an increase of >20% in IFN-γ levels after stimulation with the variant versus after stimulation with the wild-type E75. The 20% value was chosen as a cut-off for significant increase based on the assumption that if a 2-fold increase of the minimum 5% increase (defined above) is 10%, then an increase >10% should be significant if it equals at least 20%. Equal numbers of viable effectors were used in all assays. IL-2, IL-4, and IFN-γ were detected using cytokine ELISA kits (Biosource International or R&D Systems, Minneapolis, Minn.) with a sensitivity of 4-7 pg/ml (Lee et al., 2000).

Apoptosis Assays

E75- and S5K-CTL lines were activated by autologous DCs pulsed with various concentrations of E75 or S5K in the presence or absence of 100 μg/ml of CH11. For anti-CD3-mediated apoptosis, OKT3 mAb was absorbed on wells of 96-well plates overnight before addition of lymphocytes (DiSomma et al., 1999). For day 1 apoptosis assays, IL-2 was not added to the cultures. For day 4 apoptosis assays, IL-2 (300 IU/ml) was added to the cultures at 24 and 72 h after stimulation with DC-pulsed peptides. Detection of Fas-mediated apoptosis was performed in the presence or absence of the agonistic mAb CH11 (anti-Fas mAb) as described (DiSomma et al., 1999). Cells were labeled by incubation in PBS containing 0.1% Triton X-100 and 50 μg/ml propidium iodide, and the DNA content was determined by using flow cytometry.

Western Analysis

A total of $2 \times 10^6$ S5K-CD8$^+$ cells were stimulated for 96 h with E75, S5K, A7.3, or F8-1 peptides pulsed on DCs at a final concentration of 25 μg/ml. Additional controls included cells that were stimulated with T2 that had not been pulsed with peptide, or S5K cells that were not stimulated or cells that were stimulated with PHA. A total of 20 μg of protein from supernatants from 10,000 g of postnuclear detergent lysates were separated on a 12% SDS-PAGE gel and immunoblotted as described (Ward et al., 2000). Membranes were probed with monoclonal anti-actin, anti-Bcl-2 (1:500), anti-Bad (1:500), or anti-Bcl-x$_L$ (1:500) in 1% BSA-TBS containing 0.1% Tween 20 for 2 h at 25° C., and probed with peroxidase-linked sheep antimouse Ig (1:1000) in 1% BSA-TBS containing 0.1% Tween 20. Immunoreactive bands were detected by ECL as described (Ward et al., 2000).

Example 12

Molecular Modeling

To address deficiencies in the art, binding of the HER-2/neu protooncogene (HER-2), CTL epitope E75 (369-377) to HLA-A2 was examined at the atomic level. Molecular models of the E75-HLA-A2 complex indicated that the side chain of the central Ser5 (S373) points upward. Thus, the OH group can either enhance binding at the TCR via a hydrogen bond, or sterically hinder the interaction with the TCR by decreasing the affinity of the TCR for the pMHC-I. If the first hypothesis is true, then removal of the OH group should decrease the affinity of binding by the TCR and decrease signaling, hence variants in which the central Ser is replaced by Ala or Gly should be less immunogenic than wild-type E75. If the second hypothesis is true, then Ala/Gly variants should be more immunogenic than the wild-type E75. To address the requirement that variant-induced CTLs survive their encounter with the wild-type antigen, another variant was created to demonstrate that stimulation with that variant should protect responding cells from death by over-stimulation. This variant should stimulate some of the effector functions weaker than E75, and E75 should activate the variant-induced effectors. The only alternatives that would not disturb the peptide bond were positively and negatively charged side chains. Because the negatively charged amino acids Glu and Asp have bulky carboxyl groups, Ser5 was replaced with the positively charged Lys5 (variant S5K). The aminopropyl group of Lys extends farther and has a greater flexibility than the acetyl group of the Glu.

Priming with variants S5A and S5G enhanced the induction of IFN-γ and E75-specific cytolysis of CTL from two donors known to respond to E75, but the responders died faster than did the cells that had been stimulated by E75. In contrast, variant S5K induced higher levels of IFN-γ, but not of CTL activity against E75 than the E75-induced CTL (E75-CTL). In a "weak responder" to E75, S5K-induced CTL (S5K-CTL) recognized E75 with lower affinity than did E75-induced CTL. S5K-CTL survived longer than the E75-CTL, which became apoptotic at restimulation with E75. Of interest, restimulation with E75 resulted in better protection from apoptosis in the S5K-CTL than did restimulation with S5K. This protection was paralleled by higher Bcl-x$_L$ to Bad ratios and higher Bcl-2 levels than the ones induced by S5K. Thus, the side chain variants that were less activating than the wild-type antigen induced specific CTL for the E75 expressed on tumors. Such CTL were then expanded by E75, indicating that the nominal antigen or stronger agonistic variants can use priming with weak agonists to bypass induction of apoptosis.

Example 13

Generation of E75 Variants Directed by Molecular Modeling

This approach was designed to identify amino acids in E75 permissive to replacement that would be substituted without abolishing the objects of the variant peptide to induce CTL responses. Substitutions in side chains that maintain the overall conformation of the peptide backbone in the HLA-2 were deemed more likely to lead to cross-reactive antigen for wild-type antigen-specific CTL than substitutions that change the peptide backbone conformation. The E75-HLA-A2 complex was modeled by replacing the human T cell leukemia virus-1 peptide Tax with E75. The Tax peptide (Ding et al., 1999; Baker et al., 2000) shows the highest structural similarity with E75 of the models available in the databases. The Tax sequence LLFGYPVYV (SEQ ID NO. 1) is similar to that of E75:KIFGSLAFL with respect to the position of aromatic residues in P3 and P8 and the aliphatic side chain extensions in the first four and the last three amino acids (only K1 and F8 differ by an $NH_3$ and an OH group extension). The major differences rest in the central area P5 P6:YP versus SL. One Tax analog, P6A, showed even more similarity with E75 YA versus SL, with Ala and Leu differing only in the propyl side chain. This comparison allowed identification of the side chains that point upwards or sideways and are thus more likely to contact TCR.

The results show that the side chains of Lys1, Ser5, and Phe8 point out of the binding pocket of the MHC. The side chains of Phe3, Leu6, and Ala7 point toward the helical "walls" of the pocket. The models of the TCR-pMHC-I (HLA-A2) interaction predicted that of the side chains pointing away from the MHC, Ser5, Leu6, and Ala7 were most likely to contact the CDR3 (Vα+Vβ) region. Ser5 was focused on because the change induced by the removal of the hydroxyl group was likely to have the strongest effects. Ser was substituted with Ala, Gly, and Lys. These substitutions removed an HO-group (Ala), a HO—$CH_2$-group (Gly), or replaced the OH group with the aminopropyl ($CH_2$—$CH_2$—$CH_2$—$NH_3$) group. The position of the OH suggested that it was less involved in interactions with the HLA-A2. No significant changes of the MHC molecule were necessary to accommodate these modifications. Ser5 was preceded by Gly4, which because it does not have a side chain, is very flexible and may allow small accommodations in the model. The positions of Phe3 and Lys1 that precede the Ser5 seem to be unchanged among the four models. These results indicated that Ser5 is in a good structural position to allow side chain replacements in the antigenic peptide that can modify its interactions with TCR. S5A, S5G, and S5K bound to HLA-A2 with similar affinity as did E75 (Table II). In T2-stabilization assays, S5A, S5G, and S5K showed similar stabilizing ability for HLA-A2 as determined with mAb MA2.1 (Table II, legend), and similar scores for times of dissociation and ligation strengths (Table II) with those of E75 as determined using the HLA-peptide binding prediction (Parker et al., 1994) and SYFPEITHI programs (Rammensee et al., 1999).

Example 14

Increased IFN-γ-Inducing and E75-Specific CTL-Inducing Ability of the E75-Variants S5A and S5G To demonstrate modification of the E75 side chain by deletion or extension to increase or decrease the ability of the modified antigen to stimulate CTL induction and survival, several healthy donors known from previous studies were tested to produce E75-specific CTL at priming ("strong responders", donors 1 and 2) or exhibit weak CTL activity after several repeated stimulations (weak responders, donor 3). PBMC were stimulated in parallel with autologous DCs pulsed with E75 variants. Donor 1 responded with higher levels of IFN-γ at priming with variants S5K, S5G, and S5A, and lower levels of IFN-γ at priming with control variants F8Y and F8K than at priming with E75 (FIG. 8A and FIG. 8B). CTL induced by priming with E75 recognized E75 better than a CTL induced by S5K, F8Y, or F8K, whereas CTL induced by S5G and S5A recognized E75 better than CTL induced by E75. S5A and S5G induced both higher levels of IFN-γ and higher cytolytic activity than did E75. Thus, removal of the OH group correlated with higher IFN-γ induction and higher lytic activity against E75.

CTL induced by S5K secreted higher levels of IFN-γ, but their recognition of E75 was weaker. Thus, replacement of OH group with aminopropyl group had more selective effect than removal of the OH group. Extension of these results with cells from donor 2 revealed that all the E75 variants induced higher levels of IFN-γ at priming than did E75: S5K by 36%, S5A by 100%, and S5G by 64% (FIG. 8C). Significantly higher levels of IFN-γ were detected 96 h after stimulation with each variant in response to the highest dose (25 μg) of exogenously pulsed peptide in the presence of IL-2 for 2 days. Significant differences in IFN-γ induction were not observed when E75 or its variants were used at 1.0 or 5.0 μg/ml at 48 or 72 h. The E75-specific lytic activity of CTL induced by S5A was significantly higher than the lytic activity of CTL induced by E75 (FIG. 8D). The increase in lytic activity by S5A paralleled the increase in IFN-γ in response to S5A. Recognition of E75 by S5KCTL was lower than the recognition by E75-CTL. CTL induced by the E75, S5K-CTL, and S5A-CTL all recognized the indicator SKOV3.A2 tumor. To determine whether E75-specific tumor-lytic CTLs were present in the variant-induced CTL, the inventors performed cold-target inhibition of tumor lysis. Tumor lysis by S5K-CTL was inhibited less by T2-E75 than lysis by E75-CTL (FIG. 8E). This confirmation that S5A can induce both higher IFN-γ and higher lytic activity against E75 suggested that the OH group of Ser5 hindered the TCR interaction with peptide-HLA-A2 and that removal of the OH group allowed a stronger TCR activation. However, at restimulation, the number of cells stimulated by S5A and S5G dropped faster than the number of cells that had been stimulated by E75. Cells stimulated by S5K survived longer than E75-stimulated cells (FIG. 8F), suggesting that the stimulus from the $(CH_2)_3$—$NH_3$ was more effective than stimuli from the $CH_3$ or the $CH_2$—OH in maintaining the survival of responders.

TABLE II

HLA-A2 Binding Stability by E75 and its Variants[a]

| Code | Sequence | Binding Stability | Ligation[b] Strength | Change |
|---|---|---|---|---|
| E75 | KIFGSLAFL SEQ ID NO. 2 | 482 | 28 | Wild type |
| K1G | GIFGSLAFL SEQ ID NO. 3 | 138 | 28 | Positive charge→neutral |

TABLE II-continued

HLA-A2 Binding Stability by E75 and its Variants[a]

| Code | Sequence | Binding Stability | Ligation[b] Strength | Change |
|---|---|---|---|---|
| S5A | KIFGALAFL SEQ ID NO. 4 | 482 | 28 | OH→nonpolar aliphatic |
| S5G | KIFGGLAFL SEQ ID NO. 5 | 483 | 30 | OH→neutral |
| S5K | KIFGKLAFL SEQ ID NO. 6 | 482 | 29 | OH→positive charge |
| F8K | KIFSGSLAKL SEQ ID NO. 7 | 88 | 30 | Aromatic to (+) charged |
| F8Y | KIFGSLAYL SEQ ID NO. 8 | 482 | 28 | OH in aromatic residue |
| F8D | KIFGSLADL SEQ ID NO. 9 | 236 | 28 | Aromatic to (−) charged |
| A7.3 | K1FGSL(NLeu)FL SEQ ID NO. 10 | Nd[c] | Nd | 2 $CH_2$ extension of Ala[7] |
| F8-1 | K1FGSLA(Iso-Phe)L SEQ ID NO. 11 | Nd | Nd | 1 $CH_2$ deletion of Phe[8] |

[a]The binding stability is an estimate of half time of dissociation (in minutes) from HLA-A2 of peptides of the sequence listed above. The theoretical half-life of dissociation was calculated using Parker's algorithm (Parker et al., 1994) available on the world wide web at bimas.dcrt.ig.gov/molbiol/hla-bind.
[b]The ligation strength was calculated using the SYFPEITHI program (Rammensee et al., 1999). The experimentally determined mean channel fluorescence values for HLA-A2 expression on T2 cells after incubation with peptides and staining with MA.2.1 mAb were: NP = 90, E75 = 305, S5G = 295, S5A = 290, S5K = 285, K1G = 240, and F8Y = 305.
[c]nd, not done.

Example 14

Stimulation with S5K Enhanced Survival of Responding T Cells

Cancer patients are weak responders to E75 and require repeated stimulation for CTL induction. To clarify the differences between E75 and S5K in the induction of cytolysis, the inventors tested T cells from donor 3 for whom several stimulations with E75 were required to induce detectable CTL activity, but responded with IFN-γ secretion at priming (Anderson et al., 2000). S5K and E75 induced similar levels of IFN-γ at priming and at restimulation (FIG. 9A). The kinetics of induction of E75-specific CTL in relation to the number of stimulations is shown in FIG. 9B. E75 again induced higher E75-specific lytic activity than did S5K. Like donor 2, E75-stimulated cells from donor 3 declined in number after the third stimulation with antigen more than the S5K-stimulated cells (FIG. 9C). These results showed that S5K induced better survival in responders than E75. These results were confirmed in subsequent stimulation studies. In parallel studies, priming with E75 induced lower levels of Bcl-2 in CD8+ cells than did priming with S5K. There were only small differences in Fas ligand, Fas, and IL-2Rα expression between E75-stimulated and S5K-stimulated donor 3 CD8+ cells.

Example 15

S5K-Induced CTL Recognized E75 with Lower Affinity than E75-Induced CTL

Weaker recognition of E75 by the S5K-CTL raised the question of whether S5K induced smaller numbers of CTL than E75, or whether the CTL induced by S5K had lower affinity for E75 than for S5K. To address the recognition of variant-induced CTL, the ability to recognize E75 and the inducing variant was tested in parallel. S5A-CTL (donor 1) recognized S5K weaker than S5A (24% decrease), suggesting that extension of the $CH_2$ side chain in position 5 with OH and $(CH_2)_3$—$NH_3$ groups, respectively, hindered TCR recognition. Similarly, donor 3 S5K-CTL recognized E75 weaker than they recognized S5K (FIG. 10A).

To verify that S5K is recognized with lower affinity than E75 by donor 3 E75-CTL, concentration-dependent lysis was performed. E75-CTL recognized S5K with lower affinity than E75. S5K recognition was close to recognition of E75 (32 vs 41%) only at high concentrations (50 μg/ml; FIG. 10B). Similarly, S5K-CTL recognized E75 with lower affinity than S5K (FIG. 10C). These results demonstrated that the OH and aminopropyl groups selectively modulated the affinity of recognition. To address whether E75-specific CTL were present in smaller numbers in S5K-CTL, the inventors tested recognition of E75 at the same concentration (10 μg/ml) at four E:T ratios (10, 20, 30, 40). Even at the highest E:T ratio of 40:1, S5K-CTL recognized E75 (25.4% lysis) to a significantly lesser extent than did E75-CTL at an E:T ratio of 10:1 (48.2% lysis).

Example 16

S5K-CTL Recognize Endogenously Presented E75

Because S5K-CTL survived longer than E75-CTL, this suggested that S5K could be used to induce CTL-recognizing tumors. To determine whether S5K-CTL recognized endogenous E75 in cytolysis assays, cold-target inhibition of tumor lysis was performed. T2-E75 inhibited lysis of freshly isolated ovarian tumor OVA-16 (HLA-A2$^+$, HER-2$^{high}$) by 21% in an 8-h CTL assay, and by 45% in a 16-h assay (FIG. 11A and FIG. 11B). Similar inhibition (38%) was observed against SKOV3.A2 in a 16-h assay. These results indicated that S5K-CTL recognized the endogenously presented E75 and ovarian tumors overexpressing HER-2. The levels of inhibition of lysis indicative of specific recognition were similar to those levels observed with donor 2, E75-CTL, and S5K-CTL (FIG. 8E). S5K-CTL was also tested for the ability to secrete IFN-γ at an encounter with the ovarian tumor SKOV3.A2 and its HLA-A2$^-$ counterpart SKOV3. This was necessary because the tumor and responding lymphocytes shared HLA-A3. S5K cells secreted high levels of IFN-γ within 20 h, when IL-12 was used as costimulator (FIG. 11C). IFN-γ was induced even in the absence of IL-12, but at lower levels. mAb inhibition studies indicated that IFN-γ secretion was associated with recognition of HLA-A2. This indicated that present among the S5K-induced CTL was a subpopulation of cells that recognized endogenously presented E75 by cytolysis and IFN-γ secretion.

Example 17

Antiapoptotic Effects of E75 in S5K-Activated CD8$^+$ Cells

Induction of CTL by the variant S5K raised the question of whether such cells could survive an encounter with E75, since E75 is present in vivo. To address whether E75 can induce CD95-mediated apoptosis, E75-CTL and S5K-CTL were stimulated with E75 and S5K in parallel in the presence of the agonistic Ab CH11. Three days after stimulation with E75, 46% of the E75-CTL had undergone apoptosis, whereas only 15.4% of the S5K-CTL were apoptotic after stimulation with S5K. In contrast, when S5K-CTL were stimulated with S5K or E75, cells stimulated with E75 survived longer and may have increased in number as compared with the cells stimulated with S5K. Stimulation of S5K-CTL with 25 or 50 µg/ml E75 for 4 days increased the number of CD8$^+$ cells by 26 and 64%, respectively. Stimulation of the same cells with S5K$^+$ anti-Fas increased their numbers by 0.93 and 27%, respectively (FIG. 12A and FIG. 12B), but no increase in cell number was observed in the absence of CH11. Notably, S5K-CTL continued to respond to S5K with higher levels of IFN-γ, but lower levels of IL-2, than did cells treated with E75. To address whether E75 and S5K interfered with apoptosis pathways, S5K-CTL were restimulated with E75 or S5K at two different concentrations or remained unstimulated (Group 0, DC only) in the presence of CH11. Apoptosis analysis was performed at 24 and 96 h. Both E75 and S5K inhibited the residual Fas-apoptosis within 24 h and this inhibition was peptide concentration-dependent (FIG. 12C). When apoptotic cells were counted on day 4, both peptides were protective, but E75 seemed to be more protective than S5K (FIG. 12C, day 4).

To confirm the antiapoptotic effects of E75 and S5K on S5KCTL, cell cycle analysis was performed. Analysis of cells in the subG$_1$ phase (FIG. 12D) showed that 46% of the unstimulated S5K cells became apoptotic. E75 and E75+ CH11 inhibited this apoptosis by 83%. S5K had a slightly lower inhibitory effect (63% inhibition). S5K+CH11 reduced apoptosis by only 24% compared with unstimulated S5K-CTL confirming the results in FIG. 12B. The percentage of cells in G$_1$ phase (resting) was similar in both stimulated and control unstimulated cells (50±5%). The percentages of CD8$^+$ cells in S phase in cultures stimulated with E75 or S5K were also similar. Of interest, the proportion of cells in the S phase was higher in cultures stimulated by E75+CH11 than in cultures stimulated with S5K+CH11, suggesting that E75 transmitted a stronger stimulatory signal for division of S5K-CTL than their original inducing antigen. The differences between cells in the G$_2$/M phase were small compared with the unstimulated cells, and they were not considered significant. These results agree with the higher proliferation of S5K-activated CD8$^+$ cells in response to E75 than to S5K (FIG. 12A and FIG. 12B).

Apoptosis resistance in stimulated T cells at day 4 is mainly due to the intrinsic pathway (Kirchhoff et al., 2000). Because resistance to Fas-induced apoptosis was suggestive of TCR-induced protection, the effects of E75 and S5K in up-regulation of Bcl-2, Bcl-x$_L$, and Bad were investigated. Unstimulated and DC-NP-stimulated CD8$^+$ cells from S5K-CTL were used as negative controls, while S5K-CTL stimulated with the agonists A7.3 and F8-1 were used as positive controls. E75 induced a higher Bcl-x$_L$ to Bad ratio than S5K. A7.3 and F8-1 variants induced even higher Bcl-x$_L$ to Bad ratios than E75, indicating that their effects were sequence-specific (FIG. 13A). S5K was a slightly stronger up-regulator of Bcl-2 than E75. The inhibitory effects of E75 and S5K on Bad up-regulation were similar, although E75 was a slightly stronger inhibitor. These results indicated that E75-mediated protection from CD95-mediated apoptosis of S5K-CTL correlated with down-regulation of proapoptotic family members. The increase in the level of expression of Bcl-2 was considered significant compared with the up-regulation of Bcl-2 induced by a mitogen (PHA) in the same cells for 96 h. This was evident when the Bcl-2 and Bcl-x$_L$ to actin ratios were compared at stimulation with S5K and PHA vs the Bcl-2 and Bcl-x$_L$ to actin ratios in unstimulated cells (FIG. 13B). For S5K stimulation, the ratios are 1.72 (Bcl-2) and 1.32 (Bcl-x$_L$), while for PHA stimulation the ratios are 1.55 (Bcl-2) and 4.37 (Bcl-x$_L$). The increase in the levels of Bcl-2 and Bcl-x$_L$ at stimulation with PHA is comparable with the increase reported in other studies in the presence of a mitogen, but in the absence of IL-2. Increase in the Bcl-2 levels is in general observed if mitogen-activated T cells are given high doses of IL-2 (Mueller et al., 1996; Broome et al., 1995). Thus, activation and expansion of tumor-reactive CTL by the variant S5K allowed better survival of these CTL in response to the wild-type tumor antigen.

To address whether E75 and S5K stimulation affected expansion, TCR expression, and Bcl-2 expression in E75$^+$ TCR cells, S5K-CTL were stimulated with T2 cells pulsed with either E75 or S5K or not pulsed with peptide (T2-NP). The number of E75$^+$TCR cells was determined. One week later, to determine whether the affinity of the TCR for E75 was affected by the stimulation, expression of E75$^+$TCR cells was assessed both immediately after staining and after an additional 50-min incubation of dE75-stained cells in PBS (FIG. 13C, FIG. 13D and FIG. 14A). For further refinement, E75$^+$TCR expression and Bcl-2 expression were analyzed separately in two gated populations of smaller size (FW scatter: 380-600) and of larger size (FW scatter: 640-1000). In the small lymphocytes (FIG. 13C), the percentages of E75$^+$TCR cells were similar in all three stimulation groups and the E75 and S5K-stimulated S5K-CTL appeared to have similar affinities for dE75, which were stable >50 min. In contrast, in the larger lymphocytes, the percentage of E75$^+$TCR cells was higher in the E75-stimulated than in S5K-stimulated S5K cells (FIG. 13D). The affinity for E75 also seemed to be higher in the E75-stimulated group than in the S5K-stimulated group (FIG. 14A). Because E75-stimulated cells proliferated better than S5K-stimulated cells, the inventors calculated the number of E75⁺-TCR cells in each stimulated culture. The number of E75⁺-TCR cells in both small and large lymphocytes stimulated by E75 was higher than in the S5K-stimulated S5K-CTL (FIG. 14B). The percentage increase was similar to the increase observed in CD8⁺ cells (FIG. 12A and FIG. 12B). This finding confirmed that S5K-induced CTL expanded better when restimulated with E75 than when restimulated with S5K. The levels of E75⁺ TCR and Bcl-2 in the E75-stimulated S5K-CTL in the large lymphocytes were also higher than in the S5K-stimulated S5K-CTL (FIG. 14C and FIG. 14D). This suggested that stimulation of S5K-CTL with E75 resulted in changes in receptor distribution or conformation that increased the binding of dE75 as suggested by Braciale and Spencer (2000). These effects were not observed in the small E75⁺TCR lymphocytes. Bcl-2 levels were higher in the small lymphocytes after stimulation with S5K compared with E75. E75-stimulated S5K-CTL recognized E75 both as peptide and when endogenously presented by tumor. Together these results indicate that priming CD8⁺ cells with agonists for induction of cytolysis that are weaker than the nominal wild-type antigen followed by restimulation with the wild-type antigen can bypass induction of apoptosis either by the wild-type antigen (at priming) or by the weak agonist (at restimulation). This effect leads to increased survival and expansion of antitumor effectors.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein, without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,826,364
U.S. Pat. No. 3,949,064
U.S. Pat. No. 4,174,384
U.S. Pat. No. 4,284,412
U.S. Pat. No. 4,833,092
U.S. Pat. No. 4,498,766
U.S. Pat. No. 4,554,101
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,631,211
U.S. Pat. No. 4,661,913
U.S. Pat. No. 4,708,871
U.S. Pat. No. 4,714,682
U.S. Pat. No. 4,767,206
U.S. Pat. No. 4,774,189
U.S. Pat. No. 4,857,451
U.S. Pat. No. 4,989,977
U.S. Pat. No. 5,160,974
U.S. Pat. No. 5,194,392
U.S. Pat. No. 5,202,238
U.S. Pat. No. 5,440,013
U.S. Pat. No. 5,446,128
U.S. Pat. No. 5,475,085
U.S. Pat. No. 5,478,722
U.S. Pat. No. 5,480,971
U.S. Pat. No. 5,482,856
U.S. Pat. No. 5,484,719
U.S. Pat. No. 5,585,089
U.S. Pat. No. 5,612,487
U.S. Pat. No. 5,618,914
U.S. Pat. No. 5,618,920
U.S. Pat. No. 5,661,016
U.S. Pat. No. 5,663,425
U.S. Pat. No. 5,665,126
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,859,184
U.S. Pat. No. 5,914,123
U.S. Pat. No. 5,929,237
U.S. Pat. No. 5,977,438
U.S. Pat. No. 6,034,298
Anderson et al., *Clin. Cancer Res.*, 6:4192-4200, 2000.
Ausubel et al., In: *Current Protocols in Molecular Biology*, Green Pub. Assoc., Inc., and John Wiley & Sons, Inc., NY, (I):2.10.3, 1989.
Azuma et al., *J. Biol. Response Mod.*, 7(5):473-482, 1988.
Baker et al., *Immunity*, 13:475-484, 2000.
Berman et al., *Nucleic Acids Res.*, 28:235, 2000.
Bernard et al., *AIDS*, 12(16):2125-39, 1998.
Brutlag et al., *Comput. Appl. Biosci.*, 6(3):237-245, 1990.
Charini et al., *J. Immunol.*, 167:4996, 2001.
Chicz and Urban, *Immunol. Today*, 15:155-160, 1994.
Chou and Fasman, *Adv. Enzymol.*, 47:45-148, 1978.
Chou and Fasman, *Annu Rev Biochem*, 47:251-276, 1978.
Chou and Fasman, *Biochemistry*, 13(2):211-222, 1974.
Chou and Fasman, *Biochemistry*, 13(2):222-245, 1974.
Chou and Fasman, *Biophys J*, 26(3):385-399, 1979.
Ding et al., *Immunity*, 11:45, 1999.
DiSomma et al., *J. Immunol.*, 162:3851, 1999.
Falk et al. *Nature*, 351:290, 1991.
Fetrow and Bryant, *Biotechnology*, 11(4):479-84, 1993.
Fisk et al., *Int. J. Oncol.*, 10:159-169, 1997.
Fisk et al., *J. Exp. Med.*, 181:2109-2117, 1995.
Fisk et al., *J. Immunother.*, 18:197, 1995.
Freifelder, *Physical Biochemistry Applications to Biochemistry and Molecular Biology*, 2nd ed. Wm. Freeman and Co., New York, N.Y., 1982.
Garboczi et al., *Nature*, 384:134-141, 1996.
Geysen et al., *Proc. Natl. Acad. Sci. USA*, 81:3998-4002, 1984.
Gillogly et al., *FASEB J.*, 14, A147.18, 2000,
Hausman et al., *J. Immunol.*, 162:5389, 1999.
Houghten, *Proc. Natl. Acad. Sci. USA*, 82:5131-5135, 1985.
Jameson and Wolf, *Comput Appl Biosci*, 4(1):181-186, 1988.

Kirchhoff et al., *J. Immunol.*, 165:6293, 2000.
Knutson et al., *J. Clin. Invest.*, 107:477, 2001.
Krammer, *Nature*, 407:789-795, 2000
Kyte and Doolittle, *J Mol Biol*, 157(1):105-32, 1982.
Lee et al., *Oncol. Reports*, 7:455-466, 2000.
Lu and Celis, *Cancer Res.*, 15; 60(18):5223-7, 2000
Madden et al., *Cell*, 75:693-708, 1993.
Maniatis, et al., Molecular Cloning, A Laboratory Manual, Cold Spring Harbor Press, Cold Spring Harbor, N.Y., 1988.
Mitchell et al., *Ann. NY Acad. Sci.*, 690:153-166, 1993.
Mitchell et al., *J. Clin. Oncol.*, 8(5):856-869, 1990.
Morton et al., *Arch Surg*, 127:392-399, 1992.
Nociari et al., *J Immunol Methods*, 213(2):157-67, 1998.
Page et al., *Anticancer Res*, 18(4A):2313-6, 1998.
Parker et al., *J. Immunol.*, 153:163, 1994.
Peitsch et al., *Electrophoresis*, 18:498, 1997.
Peitsch et al., *Electrophoresis*, 18:498, 1997.
Rabinovich et al., *Science*, 265:1401-1402, 1994.
Rammensee et al., *Immunogenetics*, 50:213, 1999.
Ravindranath and Morton, *Intern. Rev. Immunol.*, 7: 303-329, 1991.
Remington's Pharmaceutical Sciences, 18th Ed. Mack Printing Company, 1990.
Rongcun et al., *J. Immunol.*, 163:1037-1044, 1999.
Rosenberg et al, *Hosp. Prac.*, 21:131-137, 1986.
Roy and Nicholson, *J. Exp. Med.*, F21-25, 2000.
Sambrook et al., In: *Molecular cloning*, Cold Spring Harbor Laboratory Press, Cold Spring Harbor, N.Y., 2001.
Saper et al., *J. Mol. Biol.*, 219:377, 1999.
Simon et al., *Mol. Immunol.*, 38(9):681-7, 2002.
Simpson et al., *Gastroenterology*, 115(4):849-55, 1998.
Stern and Wily, *Structure*, 2, 245-251, 1994.
Sutcliffe et al., *Science*, 219:660-666, 1984.
Takada et al., *Infection and Immunity*, 63(1):57-65, 1995.
Thomas et al., *Biochim. Biophys. Acta*, 1032: 177, 1990.
Van der Zee et al. *Eur. J. Immunol.*, 19:43-47, 1989.
Wallace et al., *Cancer Res.* 53:2358-2367, 1993.
Ward et al., *Biochemistry*, 39:10319, 2000.
Warner et al., *AIDS Res. and Human Retroviruses*, 7:645-655, 1991
Weidmann et al., *Cancer Immunol. Immunother.*, 39:1-14, 1994.
Weinberger et al., *Science*, 228:740-742, 1985.
Williams et al., *J. Exp. Med.*, 18:1531-1544, 1999.
Wolf et al., *Comput. Appl. Biosci.*, 4(1):187-191, 1988.
Yamamoto et al., *Jpn. J. Cancer Res.*, 79:866-873, 1988.
Yin et al., *J. Biol. Resp. Modif*, 8:190-205, 1989.
Zaks and Rosenberg, *Cancer Res.*, 58:4902-4908, 1998.
zum Buschenfelde et al., *J. Immunol.*, 165:4133-4140, 2000.

---

The invention claimed is:

1. An immunogenic cytotoxic T lymphocyte (CTL) peptide antigen comprising a modified E75 CTL epitope, wherein the modified E75 CTL epitope has the amino acid sequence of SEQ ID NO:2 with an amino acid substitution at position 4, position 7, or position 8, wherein the amino acid substitution is α-aminobutyric acid, norvaline or norleucine at position 4; α-aminobutyric acid, norvaline or norleucine at position 7; or isophenylalanine at position 8 of SEQ ID NO:2.

2. The peptide antigen of claim 1, wherein the amino acid at position 4 of the modified E75 CTL epitope has a longer side chain compared to the glycine at position 4 of SEQ ID NO: 2.

3. The peptide antigen of claim 1, wherein the amino acid at position 7 of the modified E75 CTL epitope has a longer side chain compared to the alanine at position 7 of SEQ ID NO: 2.

4. The peptide antigen of claim 1, wherein the amino acid at position 4 of the modified E75 CTL epitope is α-aminobutyric acid, norvaline or norleucine.

5. The peptide antigen of claim 1, wherein the amino acid at position 7 of the modified E75 CTL is α-aminobutyric acid, norvaline or norleucine.

6. The peptide antigen of claim 1, wherein position 8 of the modified E75 CTL epitope is isophenylalanine.

7. The peptide antigen of claim 1, wherein the amino acid sequence of the modified E75 epitope is SEQ ID NO:10 or SEQ ID NO:11.

8. The peptide antigen of claim 1, wherein the amino acid sequence of the modified E75 CTL epitope is selected from the group consisting of:

```
K I F Abu S L A F L;      (SEQ ID NO: 12)
K I F Nva S L A F L;      (SEQ ID NO: 13)
K I F Nle S L A F L;      (SEQ ID NO: 14)
K I F G S L Abu F L;      (SEQ ID NO: 15)
K I F G S L Nva F L;      (SEQ ID NO: 16)
K I F G S L Nle F L;      (SEQ ID NO: 10)
and
K I F G S L A isoF L.     (SEQ ID NO: 11)
```

* * * * *

SEQUENCE LISTING

```
<160> NUMBER OF SEQ ID NOS: 16

<210> SEQ ID NO 1
<211> LENGTH: 9
<212> TYPE: PRT
<213> ORGANISM: Homo sapiens

<400> SEQUENCE: 1

Leu Leu Phe Gly Tyr Pro Val Tyr Val
1               5

<210> SEQ ID NO 2
<211> LENGTH: 9
<212> TYPE: PRT
<213> ORGANISM: Homo sapiens

<400> SEQUENCE: 2

Lys Ile Phe Gly Ser Leu Ala Phe Leu
1               5

<210> SEQ ID NO 3
<211> LENGTH: 9
<212> TYPE: PRT
<213> ORGANISM: Artificial
<220> FEATURE:
<223> OTHER INFORMATION: Synthetic Peptide

<400> SEQUENCE: 3

Gly Ile Phe Gly Ser Leu Ala Phe Leu
1               5

<210> SEQ ID NO 4
<211> LENGTH: 9
<212> TYPE: PRT
<213> ORGANISM: Artificial
<220> FEATURE:
<223> OTHER INFORMATION: Synthetic Peptide

<400> SEQUENCE: 4
```

Lys Ile Phe Gly Ala Leu Ala Phe Leu
1               5

<210> SEQ ID NO 5
<211> LENGTH: 9
<212> TYPE: PRT
<213> ORGANISM: Artificial
<220> FEATURE:
<223> OTHER INFORMATION: Synthetic Peptide

<400> SEQUENCE: 5

Lys Ile Phe Gly Gly Leu Ala Phe Leu
1               5

<210> SEQ ID NO 6
<211> LENGTH: 9
<212> TYPE: PRT
<213> ORGANISM: Artificial
<220> FEATURE:
<223> OTHER INFORMATION: Synthetic Peptide

<400> SEQUENCE: 6

Lys Ile Phe Gly Lys Leu Ala Phe Leu
1               5

<210> SEQ ID NO 7
<211> LENGTH: 10
<212> TYPE: PRT
<213> ORGANISM: Artificial
<220> FEATURE:
<223> OTHER INFORMATION: Synthetic Peptide

<400> SEQUENCE: 7

Lys Ile Phe Ser Gly Ser Leu Ala Lys Leu
1               5                   10

<210> SEQ ID NO 8
<211> LENGTH: 9
<212> TYPE: PRT
<213> ORGANISM: Artificial
<220> FEATURE:
<223> OTHER INFORMATION: Synthetic Peptide

<400> SEQUENCE: 8

Lys Ile Phe Gly Ser Leu Ala Tyr Leu
1               5

<210> SEQ ID NO 9
<211> LENGTH: 9
<212> TYPE: PRT
<213> ORGANISM: Artificial
<220> FEATURE:
<223> OTHER INFORMATION: Synthetic Peptide

<400> SEQUENCE: 9

Lys Ile Phe Gly Ser Leu Ala Asp Leu
1               5

<210> SEQ ID NO 10
<211> LENGTH: 9
<212> TYPE: PRT
<213> ORGANISM: Artificial
<220> FEATURE:
<223> OTHER INFORMATION: Synthetic Peptide
<220> FEATURE:
<221> NAME/KEY: modified_res
<222> LOCATION: (7)..(7)
<223> OTHER INFORMATION: Xaa = Norleucine

<400> SEQUENCE: 10

Lys Ile Phe Gly Ser Leu Xaa Phe Leu
1               5

<210> SEQ ID NO 11
<211> LENGTH: 9
<212> TYPE: PRT
<213> ORGANISM: Artificial
<220> FEATURE:
<223> OTHER INFORMATION: Synthetic Peptide
<220> FEATURE:
<221> NAME/KEY: modified_res
<222> LOCATION: (8)..(8)
<223> OTHER INFORMATION: Xaa = Isophenylalanine

<400> SEQUENCE: 11

Lys Ile Phe Gly Ser Leu Ala Xaa Leu
1               5

<210> SEQ ID NO 12
<211> LENGTH: 9
<212> TYPE: PRT
<213> ORGANISM: Artificial
<220> FEATURE:
<223> OTHER INFORMATION: Synthetic Peptide
<220> FEATURE:
<221> NAME/KEY: modified_res
<222> LOCATION: (4)..(4)
<223> OTHER INFORMATION: Xaa = 2-Aminobutyric acid

<400> SEQUENCE: 12

Lys Ile Phe Xaa Ser Leu Ala Phe Leu
1               5

<210> SEQ ID NO 13
<211> LENGTH: 9
<212> TYPE: PRT
<213> ORGANISM: Artificial
<220> FEATURE:
<223> OTHER INFORMATION: Synthetic Peptide
<220> FEATURE:
<221> NAME/KEY: modified_res
<222> LOCATION: (4)..(4)
<223> OTHER INFORMATION: Xaa = Norvaline

<400> SEQUENCE: 13

Lys Ile Phe Xaa Ser Leu Ala Phe Leu
1               5

<210> SEQ ID NO 14
<211> LENGTH: 9
<212> TYPE: PRT
<213> ORGANISM: Artificial
<220> FEATURE:
<223> OTHER INFORMATION: Synthetic Peptide
<220> FEATURE:
<221> NAME/KEY: modified_res
<222> LOCATION: (4)..(4)
<223> OTHER INFORMATION: Xaa = Norleucine

<400> SEQUENCE: 14

Lys Ile Phe Xaa Ser Leu Ala Phe Leu
1               5

<210> SEQ ID NO 15
<211> LENGTH: 9
<212> TYPE: PRT
<213> ORGANISM: Artificial

-continued

```
<220> FEATURE:
<223> OTHER INFORMATION: Synthetic Peptide
<220> FEATURE:
<221> NAME/KEY: modified_res
<222> LOCATION: (7)..(7)
<223> OTHER INFORMATION: Xaa = 2-Aminobutyric acid

<400> SEQUENCE: 15

Lys Ile Phe Gly Ser Leu Xaa Phe Leu
1               5

<210> SEQ ID NO 16
<211> LENGTH: 9
<212> TYPE: PRT
<213> ORGANISM: Artificial
<220> FEATURE:
<223> OTHER INFORMATION: Synthetic Peptide
<220> FEATURE:
<221> NAME/KEY: modified_res
<222> LOCATION: (7)..(7)
<223> OTHER INFORMATION: Xaa = Norvaline

<400> SEQUENCE: 16

Lys Ile Phe Gly Ser Leu Xaa Phe Leu
1               5
```